US012683022B2

(12) United States Patent
Shimizu et al.

(10) Patent No.: US 12,683,022 B2
(45) Date of Patent: Jul. 14, 2026

(54) MEDICAL SYSTEM

(71) Applicant: Topcon Corporation, Tokyo (JP)

(72) Inventors: Hitoshi Shimizu, Tokyo (JP); Hisashi Tsukada, Hachioji (JP)

(73) Assignee: TOPCON CORPORATION, Tokyo (JP)

( * ) Notice: Subject to any disclaimer, the term of this patent is extended or adjusted under 35 U.S.C. 154(b) by 292 days.

(21) Appl. No.: 17/641,107

(22) PCT Filed: Jun. 1, 2020

(86) PCT No.: PCT/JP2020/021523
§ 371 (c)(1),
(2) Date: Mar. 8, 2022

(87) PCT Pub. No.: WO2021/049103
PCT Pub. Date: Mar. 18, 2021

(65) Prior Publication Data
US 2022/0336095 A1     Oct. 20, 2022

(30) Foreign Application Priority Data
Sep. 12, 2019     (JP) ................................. 2019-165875

(51) Int. Cl.
*G16H 10/60*          (2018.01)
*A61B 3/117*          (2006.01)
(Continued)

(52) U.S. Cl.
CPC ............. *G16H 40/67* (2018.01); *A61B 3/117* (2013.01); *A61B 3/135* (2013.01); *A61B 3/14* (2013.01);
(Continued)

(58) Field of Classification Search
CPC ........ G16H 40/67; G16H 10/60; A61B 3/117; A61B 3/135; A61B 3/14; A61B 5/0022; A61B 5/117
See application file for complete search history.

(56) References Cited

U.S. PATENT DOCUMENTS 7,523,505 B2 *    4/2009   Menschik .............. G16H 10/60
                                                                           705/3
8,498,884 B2 *    7/2013   Maitland ................ G16H 10/60
                                                                           713/193
(Continued)

FOREIGN PATENT DOCUMENTS

JP          2002197199 A   *   7/2002
JP          2002-306430 A       10/2002
(Continued)

OTHER PUBLICATIONS

Japanese Office Action issued Sep. 19, 2023 in corresponding Japanese Patent Application No. 2019-165875 (with machine-generated English translation), 9 pages.
(Continued)

*Primary Examiner* — Jason S Tiedeman
*Assistant Examiner* — Jonathan C Edouard
(74) *Attorney, Agent, or Firm* — XSENSUS LLP

(57) ABSTRACT
A medical system of an aspect example includes a portable data storage, first information processing equipment, and telecommunication equipment. Medical information is stored in the portable data storage. The medical information includes authentication information of a subject who has undergone a medical examination and examination data acquired from the subject by the medical examination. The first information processing equipment is connected to a telecommunication network. The telecommunication equipment is configured to transmit at least part of the medical information stored in the portable data storage that has been
(Continued)

moved to an available area of the telecommunication network, to the first information processing equipment via the telecommunication network.

8 Claims, 27 Drawing Sheets

(51) Int. Cl.

| | |
|---|---|
| *A61B 3/135* | (2006.01) |
| *A61B 3/14* | (2006.01) |
| *A61B 5/00* | (2006.01) |
| *A61B 5/117* | (2016.01) |
| *G16H 40/67* | (2018.01) |

(52) U.S. Cl.
CPC ............ *A61B 5/0022* (2013.01); *A61B 5/117* (2013.01); *G16H 10/60* (2018.01)

(56) References Cited

U.S. PATENT DOCUMENTS

| | | | | |
|---|---|---|---|---|
| 9,129,099 | B1 * | 9/2015 | Paruchuri ............... | G06F 21/30 |
| 9,760,681 | B2 * | 9/2017 | Douglass ............... | G16H 10/60 |
| 10,204,704 | B1 * | 2/2019 | Wurst ................... | G16H 10/20 |
| 2003/0225596 | A1 | 12/2003 | Richardson et al. | |
| 2008/0140572 | A1 * | 6/2008 | Jackson ................ | G16H 10/65 |
| | | | | 705/51 |
| 2010/0286488 | A1 * | 11/2010 | Cohen ................... | G16H 10/65 |
| | | | | 600/300 |
| 2013/0290632 | A1 * | 10/2013 | Kumar .................. | G06Q 10/10 |
| | | | | 711/115 |
| 2014/0249854 | A1 * | 9/2014 | Moore .................. | G16H 10/60 |
| | | | | 705/3 |
| 2015/0085252 | A1 | 3/2015 | Fujimura et al. | |

| | | | | |
|---|---|---|---|---|
| 2016/0345822 | A1 | 12/2016 | Fujimura et al. | |
| 2017/0007762 | A1 * | 1/2017 | Hayter ............... | A61B 5/14532 |
| 2017/0337332 | A1 * | 11/2017 | Duma ................... | G16H 10/65 |

FOREIGN PATENT DOCUMENTS

| | | | | | | |
|---|---|---|---|---|---|---|
| JP | 2002330930 | A | * | 11/2002 | | |
| JP | 2006-271763 | A | | 10/2006 | | |
| JP | 2006343865 | A | * | 12/2006 | | |
| JP | 2007-328552 | A | | 12/2007 | | |
| JP | 2009-211236 | A | | 9/2009 | | |
| JP | 2010113504 | A | * | 5/2010 | | |
| JP | 4572680 | B2 | * | 11/2010 | .......... | G06F 19/322 |
| JP | 2011186580 | A | * | 9/2011 | | |
| JP | 2013081601 | A | * | 5/2013 | | |
| JP | 2013-248376 | A | | 12/2013 | | |
| JP | 2014-26410 | A | | 2/2014 | | |
| JP | 2014029637 | A | * | 2/2014 | | |
| JP | 2015-210765 | A | | 11/2015 | | |
| JP | 2016-129058 | A | | 7/2016 | | |
| JP | 2017012519 | A | * | 1/2017 | | |
| JP | 2018-27260 | A | | 2/2018 | | |
| JP | 2019-16080 | A | | 1/2019 | | |
| JP | 2019-088917 | A | | 6/2019 | | |
| JP | 2019101678 | A | * | 6/2019 | | |
| WO | WO-2006119396 | A2 | * | 11/2006 | ............ | G16H 10/60 |
| WO | WO-2019072818 | A1 | * | 4/2019 | ......... | G06K 7/10366 |

OTHER PUBLICATIONS

Japanese Office Action issued Nov. 14, 2023 in corresponding Japanese Patent Application No. 2019-165875 (with machine-generated English translation), 6 pages.

International Search Report and Written Opinion mailed on Aug. 25, 2020, received for PCT Application PCT/JP2020/021523, Filed on Jun. 1, 2020, 8 pages including English Translation.

* cited by examiner

START

S1  ACQUIRE EXAMINATION DATA

S2  GENERATE AUTHENTICATION INFORMATION

S3  GENERATE TIME INFORMATION

S4  STORE MEDICAL INFORMATION IN PORTABLE DATA STORAGE

S5  ANY MORE SUBJECTS?

Yes

No

S6  MOVE TO RELAY SITE

A

MEDICAL SYSTEM

CROSS-REFERENCE TO RELATED APPLICATIONS

This application is a national stage (under 35 U.S.C. 371) of International Patent Application No. PCT/JP2020/021523, filed Jun. 1, 2020, claiming priority to Japanese Patent Application No. 2019-165875, filed Sep. 12, 2019, both of which are herein incorporated by reference in their entirety.

TECHNICAL FIELD

The present disclosure relates to a medical system.

BACKGROUND OF THE INVENTION

There are cases in which medical examinations or treatments are conducted outside of medical institutions, such as visiting medical examinations, mobile medical examinations and visiting medical services. These types of medical services are collectively referred to as "on-site examinations" herein. The technologies disclosed in the following documents are known as technologies that can be used for on-site examinations: Japanese Unexamined Patent Application Publication No. 2002-306430, Japanese Unexamined Patent Application Publication No. 2006-271763, Japanese Unexamined Patent Application Publication No. 2014-26410, Japanese Unexamined Patent Application Publication No. 2018-27260, and Japanese Unexamined Patent Application Publication No. 2019-16080.

These conventional technologies are based on the premise that medical equipment used at on-site locations is directly or indirectly connected to a telecommunication line. In other words, these conventional technologies are based on the premise that on-site examinations are conducted in areas where network environment (telecommunication environment) is good.

BRIEF SUMMARY OF THE INVENTION

However, also considered are cases where on-site examinations are conducted in areas with poor network environment. Examples of such areas include depopulated areas, undeveloped areas, disaster-stricken areas, indigenous people residential areas, and developing countries. It is difficult to use the aforementioned conventional technologies for on-site examinations conducted in these areas.

Some may think that the use of telecommunication satellites can be a possible solution; however, this is not practical in terms of cost and data traffic because the data size of medical information such as medical images is very large. In addition, it is also problematic from the perspective of protection of personal information.

An object of the present disclosure is to provide a technology utilizable for on-site examinations conducted in areas with poor network environment.

Some aspect examples disclose a medical system that includes a portable data storage, first information processing equipment, and telecommunication equipment. Medical information is stored in the portable data storage. The medical information includes authentication information of a subject who has undergone a medical examination and examination data acquired from the subject by the medical examination. The first information processing equipment is connected to a telecommunication network. The telecommunication equipment is configured to transmit at least part of the medical information stored in the portable data storage that has been moved to an available area of the telecommunication network, to the first information processing equipment via the telecommunication network. The medical system of some aspect examples may further include second information processing equipment that is located in the available area and includes the telecommunication equipment and a reception device that receives information stored in the portable data storage. In some aspect examples, the portable data storage may be a storage device in a mobile device, and the telecommunication equipment may be a telecommunication device in the mobile device. In some aspect examples, the telecommunication equipment may transmit the authentication information to the first information processing equipment, and the first information processing equipment may include a medical information database configured to manage at least authentication information and examination data using subject identifiers; and a first comparison processor configured to compare the authentication information transmitted from the telecommunication equipment with the authentication information managed by the medical information database. In some aspect examples, if the first comparison processor obtains a comparison result that the medical information database does not contain authentication information corresponding to the authentication information transmitted from the telecommunication equipment, the telecommunication equipment may transmit examination data associated with this to the first information processing equipment, and the first information processing equipment may store this examination data in the medical information database. In some aspect examples, if the comparison result is obtained, the first information processing equipment may issue an identifier, associate this identifier with the authentication information and the examination data transmitted from the telecommunication equipment, and store the authentication information and the examination data associated with the identifier in the medical information database. In some aspect examples, if the comparison result is obtained, the first information processing equipment may transmit, to the telecommunication equipment, the identifier issued and the authentication information transmitted from the telecommunication equipment, the telecommunication equipment may transmit, to the first information processing equipment, examination data corresponding to the authentication information transmitted from the first information processing equipment, selected from among examination data stored in the portable data storage, and the identifier transmitted from the first information processing equipment, and the first information processing equipment may store the examination data transmitted from the telecommunication equipment in the medical information database by referring to the identifier transmitted from the telecommunication equipment. In some aspect examples, the examination data transmitted from the telecommunication equipment to the first information processing equipment may be erased from the portable data storage. In some aspect examples, the telecommunication equipment may transmit time information together with the authentication information to the first information processing equipment, the medical information database may manage at least authentication information, examination data, and examination history using subject identifiers, and the first information processing equipment may include a second comparison processor configured to compare the time information with the medical information database. In some aspect examples, the second comparison processor may perform comparison of the time information with the medical information database if the first comparison processor obtains a comparison result that the medical information database contains authentication information corresponding to the authentication information transmitted from the telecommunication equipment. In some aspect examples, if the second comparison processor obtains a comparison result that the medical information database does not contain examination history corresponding to the time information, the telecommunication equipment may transmit examination data associated with the time information to the first information processing equipment, and the first information processing equipment may store this examination data in the medical information database. In some aspect examples, the first information processing equipment may update examination history based on the time information. In some aspect examples, the examination data transmitted from the telecommunication equipment to the first information processing equipment may be erased from the portable data storage. In some aspect examples, if the second comparison processor obtains a comparison result that the medical information database contains examination history corresponding to the time information, examination data associated with the time information may be erased from the portable data storage. The medical system of some aspect examples may further include a time information generation processor configured to generate time information corresponding to a medical examination performed on a subject. In some aspect examples, the time information generation processor may generate the time information that includes a date on which the medical examination is performed on the subject. In some aspect examples, the time information generation processor may generate the time information that includes a date on which at least part of medical information is read out from the portable data storage for providing the telecommunication equipment with the at least part of medical information. In some aspect examples, the time information generation processor may generate the time information that includes a date on which the telecommunication equipment transmits at least part of medical information to the first information processing equipment. In some aspect examples, the telecommunication equipment may transmit each authentication information stored in the portable data storage to the first information processing equipment, and the first comparison processor may compare each authentication information transmitted from the telecommunication equipment with the medical information database. The medical system of some aspect examples may further include a medical examination apparatus, wherein examination data acquired by the medical examination apparatus may be stored in the portable data storage. In some aspect examples, the medical examination apparatus may be an ophthalmic apparatus. In some aspect examples, the ophthalmic apparatus may be a slit lamp microscope. In some aspect examples, the slit lamp microscope may include a scanner configured to scan an anterior segment of a subject's eye to collect an image group, and the examination data may include the image group. The medical system of some aspect examples may further include an authentication information generation processor configured to generate authentication information corresponding to a medical examination performed on a subject. In some aspect examples, the authentication information generation processor may acquire biological information of a subject. In some aspect examples, the authentication information generation processor may acquire an anterior eye segment image as the biological information.

DETAILED DESCRIPTION OF THE INVENTION

Figure 1:
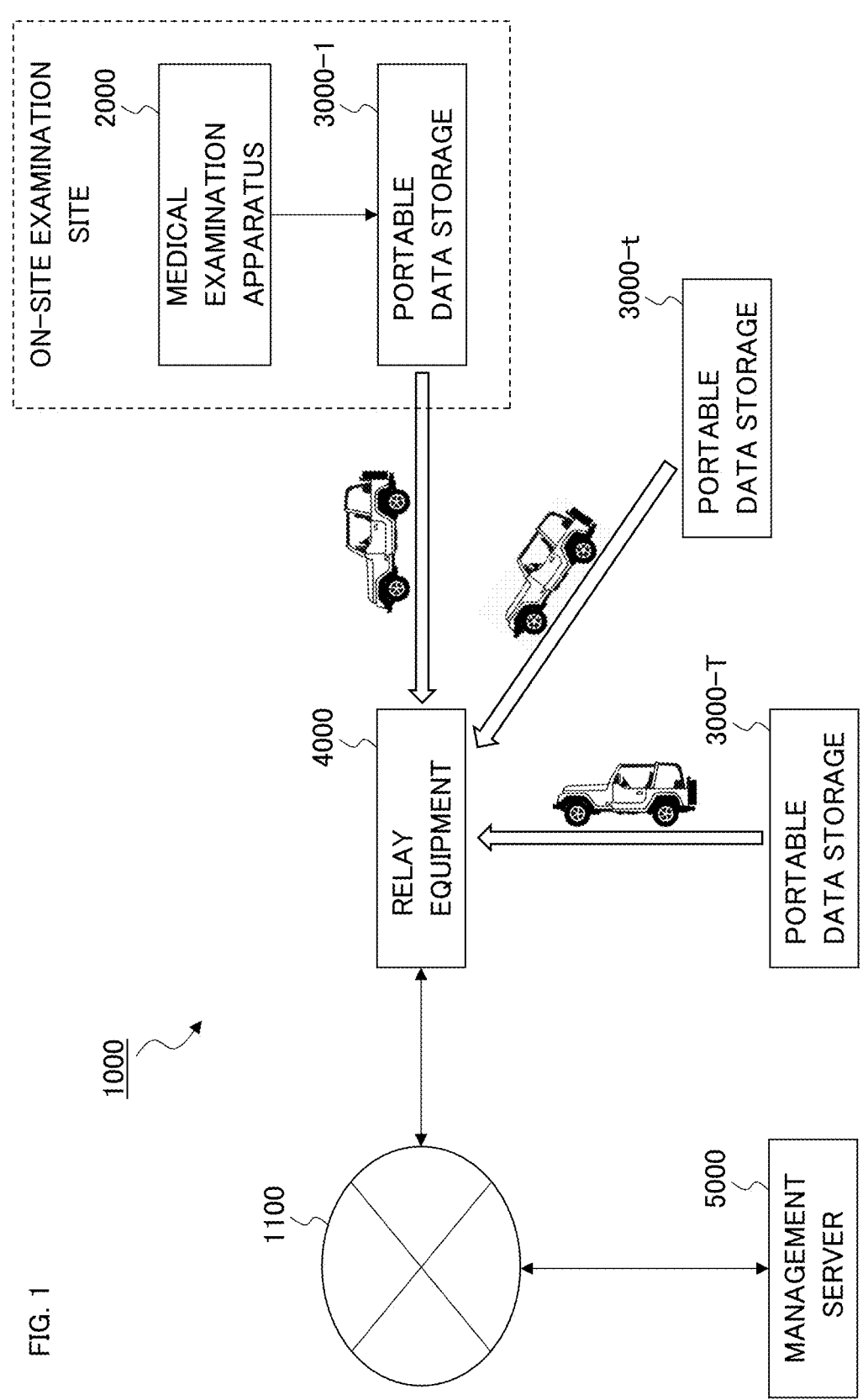
FIG. 1 is a schematic diagram illustrating the configuration of the medical system according to the aspect example.

Some aspect examples will be described in detail with referring to the drawings. It should be noted that any known techniques or technologies such as any of the matters or items disclosed in the documents cited herein may be combined with or incorporated in the aspect examples.

The medical system of the aspect examples can be used not only for on-site examinations in areas where the network environment is favorable, that is, where information (medical information, etc.) handled by the system can be appropriately communicated (transmitted and received), but also for on-site examinations in areas where the network environment is not favorable. Although the field of application of the medical system of the aspect examples described below is on-site examinations, the fields of application thereof are not limited to on-site examinations and the system may be applied to any other medical fields within the scope of the present disclosure.

The medical system of the aspect examples includes, at least, a portable data storage (mobile data storage), first information processing equipment, and telecommunication equipment. The portable data storage and the telecommunication equipment may each be separated devices, or both may be incorporated into a single device. In an example of the former case, the portable data storage is a hard disk drive carried by an examiner (a person who conducts medical examinations) for on-site examinations, while the telecommunication equipment is a computer of non-portable type. In an example of the latter case, the portable data storage is a storage device (memory) incorporated in a mobile device (mobile information terminal), while the telecommunication equipment is a telecommunication device (telecommunication circuit, antenna, etc.) incorporated in the same mobile device.

The portable data storage retains information acquired during on-site examinations. The number of pieces of portable data storages in the medical system is freely selected. Various kinds of medical information are stored in the portable data storage. The portable data storage retains various types of medical information. In some typical examples, authentication information of each subject who has undergone a medical examination in the on-site examinations and examination data acquired from each subject by a medical examination are stored in the portable data storage. The authentication information and the examination data stored in the portable data storage are associated with each other using any known technique. Information stored in the portable data storage are not limited to these kinds. For example, time information about execution of a medical examination may be stored in the portable data storage.

The portable data storage is a device configured to retains digital data that can be processed by a computer, also called a memory, a storage device, or the like. The type of the portable data storage is freely selected. For example, the portable data storage may be any of a non-volatile memory, a volatile memory, a combination of a non-volatile memory and a volatile memory, a dynamic memory, a static memory, a combination of a dynamic memory and a static memory, a read-write memory, a read-only memory, and a combination of a read-write memory and a read-only memory. The storage capacity of the portable data storage is also freely determined. The storage device technology applied to the portable data storage is also freely selected, and may be any of a semiconductor memory, a magnetic storage, an optical storage, a magneto-optical storage, and a combination of any two or more of these, for example.

The portable data storage may or may not be part of a device having a telecommunication function. For example, the portable data storage may be any of the following: a storage device by itself; a storage device incorporated in a telecommunication device (e.g., a mobile device such as a smartphone); a storage device incorporated in a device having a telecommunication function (e.g., a medical examination device, a mobile computer); and a storage device incorporated in a device without a telecommunication function (e.g., a medical examination device, a computer). In any case, portable data storage alone or a device in which portable data storage is incorporated may be referred to simply as "portable data storage" herein.

The first information processing equipment includes one or more computers that can be connected to a telecommunication network. For example, the first information processing equipment includes a database (medical information database) that manages medical information such as examination data collected by on-site examinations, and is configured to perform various information processing of medical information. The method and system of the telecommunication network employed in the aspect examples are freely selected.

The telecommunication equipment includes a computer that can be connected to the same telecommunication network as the first information processing equipment. The first information processing equipment and telecommunication equipment can communicate with each other using the telecommunication network as a two-way communication. Each of the first information processing equipment and the telecommunication equipment in some typical examples is connected to the telecommunication network as wired connection, while at least one of the first information processing equipment and the telecommunication equipment in some examples may be wirelessly connected to the telecommunication network.

The telecommunication equipment, by itself or through other telecommunication equipment, forms an available area of a telecommunication network. In some aspect examples, the available area means the area within which information retained in the portable data storage can be transmitted to a device connected to the telecommunication network (e.g., the first information processing equipment). The aspect of the connection to the telecommunication network in the available area may be wired connection and/or wireless connection.

In some examples of the wired connection, one end of a connection cable is connected to the telecommunication equipment and the other end is connected to the portable data storage. The telecommunication equipment and the portable data storage can send and receive information through the communication cable between them. For example, in the case where the portable data storage is a storage device alone, the portable data storage wiredly connected to the telecommunication equipment is treated as a peripheral device of the telecommunication equipment. As a concrete example, when the portable data storage includes a hard disk drive, the portable data storage wiredly connected to the telecommunication equipment can be used as an external hard disk drive of the telecommunication equipment. The same or like configuration can be adopted for portable data storage of other types.

In some examples of the wireless connection, the portable data storage is equipped with a wireless communication function or is used in conjunction with telecommunication equipment having a wireless communication function. The portable data storage that has been moved into the available area can use the wireless communication function to establish wireless communication with the telecommunication equipment. For example, when the portable data storage includes a memory of a mobile device, wireless communication is established between this mobile device and the telecommunication equipment. The same or like configuration can be adopted for portable data storage of other types.

When the portable data storage has been moved into the available area, the telecommunication equipment becomes capable of reading out at least part of the medical information retained in the portable data storage and transmit it to the first information processing equipment via the telecommunication network.

According to the medical system configured in this way, medical information collected by on-site examinations conducted outside the available area of the telecommunication network can be stored in the portable data storage, and when the portable data storage is moved into the available area, the medical information can be read from the portable data storage and sent to the first information processing equipment through the telecommunication network. This makes it possible to transmit the information obtained by on-site examinations conducted in an area with a poor communication environment, from an area with a good communication environment. As mentioned above, the conventional technologies are based on the premise that on-site examinations are conducted in an available area of a telecommunication network, so that they cannot be used in an area where network environment is poor and are not designed to be used in an area with a poor network environment from the very first.

Some aspect examples of such a medical system will be described below. These aspect examples provide some concrete configurations of the medical system described above, as well as some means of addressing some of the problems that are anticipated to arise when managing medical information obtained in areas with poor network environments.

The anticipated problems may include duplication of subjects and duplication of examination dates. For example, in on-site examinations conducted in an area with a poor network environment (depopulated area, undeveloped area, disaster-stricken area, indigenous people residential area, developing country, or the like), it can be anticipated that personal identification information is not assigned to each subject. In such a case, there is a risk of conducting the same examination multiple times for the same subject on the same day. In addition, it can also be anticipated that multiple examiners conduct on-site examinations while traveling around the same area. In such a case, there is a risk of conducting the same examination multiple times for the same subject on different days. The possibility of such examination duplication problems is considered to be particularly high in on-site examinations for nomadic people or the like. The following aspect examples propose novel methods and techniques in order to address these problems.

The "processor" as used in the aspect examples described below includes a circuit or circuitry such as a central processing unit (CPU), a graphics processing unit (GPU), an application specific integrated circuit (ASIC), or a programmable logic device (PLD). Examples of the PLD include a simple programmable logic device (SPLD), a complex programmable logic device (CPLD), and a field programmable gate array (FPGA). For example, the processor loads and executes a program and data stored in a memory circuit or a data storage for implementing the functions according to a corresponding aspect example. The processor may include a circuit (circuitry) used for artificial intelligence or cognitive computing. The processor of some typical examples may include a computer system trained and configured through machine learning.

Some aspect examples are described below. Any modification (addition, replacement, substitution, omission, etc.) of any of the aspect examples may be made based on any known technology or technique. It is also possible to at least partially combine any two or more of these aspect examples. Any modification of such a combination may be made based on any known technology or technique.

<First aspect> The first aspect can be employed, for example, in the case where a portable data storage does not have a telecommunication function, or in the case where a portable data storage has a telecommunication function while this telecommunication function is not used for direct connection to a telecommunication network. Note that these are not the only examples to which the present aspect can be applied.

The medical system of the present aspect includes, in addition to a portable data storage, first information processing equipment, and telecommunication equipment, second information processing equipment installed in an available area of a telecommunication network. The second information processing equipment functions as relay equipment configured to transfer medical information retained in the portable data storage to the first information processing equipment.

In some typical examples, the portable data storage is carried to an area where network environment is poor by a vehicle or other means, and medical information collected by on-site examinations conducted in the area is stored in the portable data storage. The location where on-site examinations are conducted is sometimes referred to as an on-site examination site. The portable data storage retaining the medical information is carried from the on-site examination site to a telecommunication network available area by a vehicle or other means, and connected to the relay equipment. The aspect of the connection between the relay equipment and the portable data storage is freely selected. The connection aspect of some examples may be a wired or wireless connection. In some other examples, a recording media (storage media) in the portable data storage may be removed from the portable data storage and then connected to the relay equipment (or connected to a drive device that is a peripheral equipment of the relay equipment). In the case of wireless connection between the relay equipment and the portable data storage or other cases, the communication function of the portable data storage may be used. The number of pieces of portable data storage included in the medical system of the present aspect example is freely selected, and the number of pieces of relay equipment is also freely selected.

An example of the configuration of the medical system of the present aspect example is illustrated in FIG. 1. The medical system 1000 of this example includes the T pieces of portable data storage 3000-*t*, the (one or more) relay equipment 4000, and the management server 5000. Here, the number "T" is a positive integer greater than or equal to 1, and "*t*" is a positive integer less than or equal to "T". In the following, any one of the T pieces of portable data storage 3000-*t* is sometimes denoted by the reference character "3000". The relay equipment 4000 and the management server 5000 can communicate with each other in a bidirectional manner via the telecommunication network 1100. The relay equipment 4000 is an example of the second information processing equipment, and the management server 5000 is an example of the first information processing equipment.

The medical system 1000 may further include the medical examination apparatus 2000. The medical examination apparatus 2000 of some typical examples is carried to the on-site examination site together with the portable data storage 3000 and is used to perform examinations on subjects to obtain examination data. The medical examination device 2000 of some examples may be a non-portable device installed at an on-site examination site.

The number of the medical examination apparatuses 2000 included in the medical system 1000 is freely selected. In some examples, one or more medical examination apparatuses 2000 are prepared for one portable data storage 3000. In the case where two or more medical examination apparatuses 2000 are provided for one portable data storage 3000, these medical examination apparatuses 2000 may be of the same kind or of different kinds.

The medical examination apparatus 2000 may be a device of any kind that can be used for medical examination. The medical examination apparatus 2000 of some examples may be an ophthalmic apparatus. Ophthalmic apparatuses include ophthalmic measurement apparatuses and ophthalmic imaging apparatuses. An ophthalmic measurement apparatus is an apparatus used for measuring characteristics of eyes.

Examples of ophthalmic measurement apparatuses include visual acuity measurement apparatuses, ocular refractometry apparatuses (refractometers, keratometers), tonometers, specular microscopes (corneal endothelium cell measurement apparatuses), wave front analyzers (higher-order aberration measurement apparatuses), ocular axial length measurement apparatuses, visual field measurement apparatuses (perimeters), optical coherence tomography (OCT) apparatuses used for obtaining information such as morphological information and size information of eyes by applying OCT techniques.

An ophthalmic imaging apparatus is an apparatus used for obtaining images of eyes. The types of ophthalmic imaging apparatuses include slit lamp microscopes, fundus cameras (retinal cameras), scanning laser ophthalmoscopes (SLOs), and OCT apparatuses used for imaging the morphology and/or the function of fundi and/or anterior segments of eyes.

The present aspect example describes, as an example of the medical examination apparatus 2000, a slit lamp microscope that is one of the most widely and frequently used apparatus among various kinds of ophthalmic apparatuses. A slit lamp microscope is used for illuminating a subject's eye with slit light and observing and/or photographing the illuminated cross section from an oblique or side position with a microscope. One of the main uses of a slit lamp microscope is observation of anterior eye segments. In anterior eye segment observation, a doctor observes an entire anterior eye segment while moving the focal position and the area illuminated by slit light, thereby determining the presence or absence of abnormality. Acquisition of an adequate image using a slit lamp microscope requires fine and complicated operations such as illumination angle adjustment and photographing angle adjustment. It is thought to be desired that the present aspect example employs a slit lamp microscope configured to be capable of acquiring high quality images even when the examiner is not skilled in operating slit lamp microscope because it is supposed that examinations are conducted at various on-site examination sites. In light of these circumstances, the present aspect example uses the slit lamp microscope described below. Another reason for using a slit-lamp microscope in the present aspect example is that relatively large number of people in areas with poor network environments are thought to suffer from cataracts or other diseases while visual abnormalities have significant negative impacts on people's everyday lives.

The medical examination apparatus 2000 is not limited to the slit lamp microscope described below, nor is it limited to a slit lamp microscope or an ophthalmic apparatus. In addition, the medical examination apparatus 2000 is not limited to an ophthalmic apparatus, and may be any kind of apparatus usable in any medical department. For example, the medical examination apparatus 2000 may be an X-ray diagnostic apparatus, an X-ray CT scanner, an ultrasound diagnostic apparatus, an endoscope, or the like.

Figure 2:
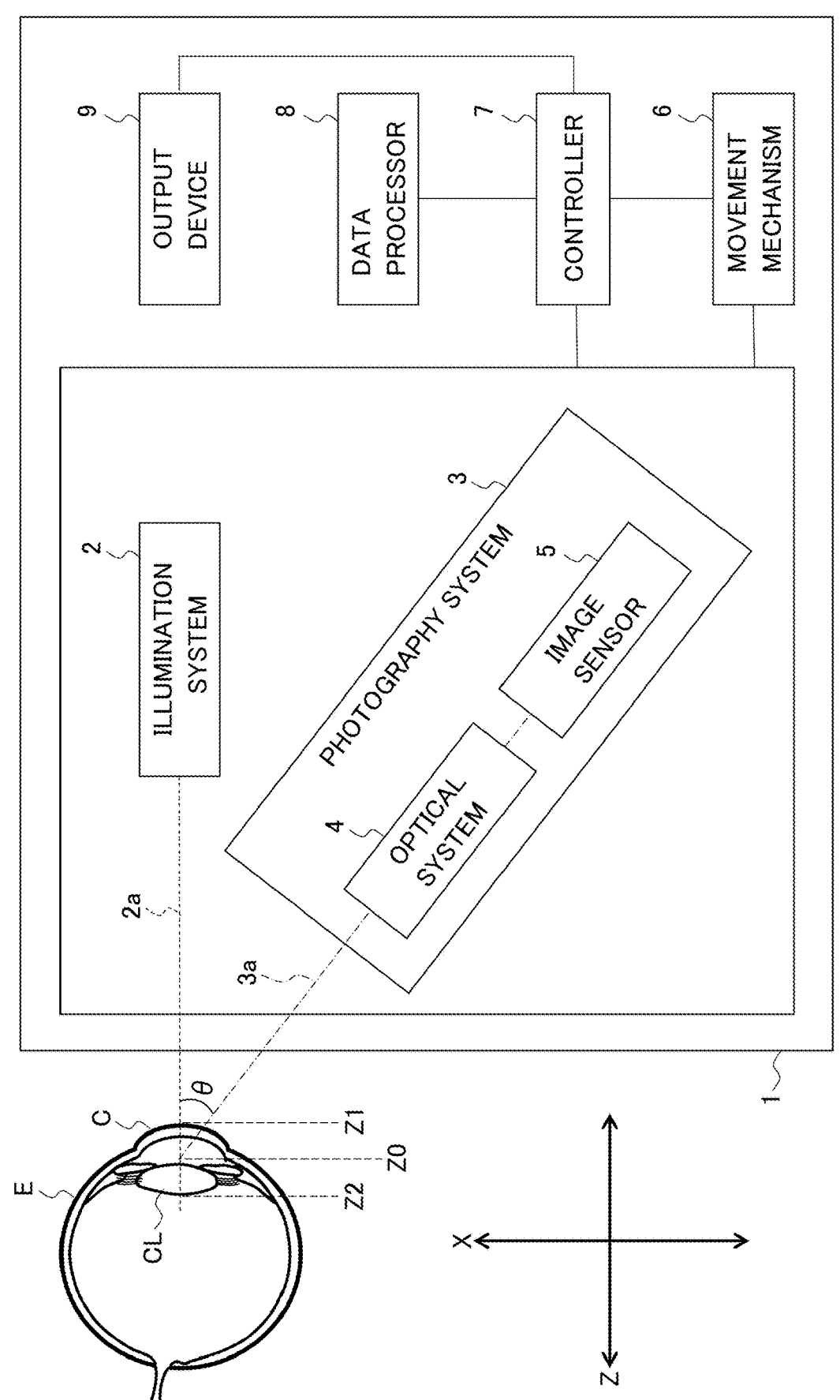
FIG. 2 is a schematic diagram illustrating the configuration of the medical system according to the aspect example.

FIG. 2 shows an example of a slit lamp microscope used as the medical examination apparatus 2000. This slit lamp microscope 1 is used for photographing the anterior segment of the subject's eye E and includes the illumination system 2, the photography system 3, the movement mechanism 6, the controller 7, the data processor 8, and the output device 9. The reference character C denotes the cornea of the subject's eye E, and the reference character CL denotes the crystalline lens. The slit lamp microscope 1 may further include freely selected element of known slit lamp microscopes.

The slit lamp microscope 1 may be either one of a single apparatus or a system including two or more apparatuses. In some examples of the latter, the slit lamp microscope 1 may include a main apparatus, a computer, and a communication device. The main apparatus may include the illumination system 2, the photography system 3, and the movement mechanism 6, the computer may include the controller 7, the data processor 8, and the output device 9, and the communication device may perform communication between the main apparatus and the computer. The computer may be provided together with the main apparatus or may be provided on a network.

The illumination system 2 projects slit light onto the anterior segment of the subject's eye E. The reference character 2*a* denotes the optical axis of the illumination system 2 (illumination optical axis). The illumination system 2 may have the same or similar configuration as or to illumination systems of conventional slit lamp microscopes. For example, the illumination system 2 includes an illumination light source, a positive lens, a slit forming member, and an objective lens in the order from the side far from the subject's eye E (not shown in the drawings).

The illumination light source outputs (emits) illumination light. The illumination system 2 may include a plurality of illumination light sources. For example, the illumination system 2 may include both an illumination light source that outputs continuous light and an illumination light source that outputs flash light. Further, the illumination system 2 may include both an illumination light source for anterior segment illumination and an illumination light source for posterior segment illumination. Furthermore, the illumination system 2 may include two or more illumination light sources with mutually different output wavelengths. The illumination system 2 of some typical examples includes a visible light source as an illumination light source. The illumination system 2 may also include an infrared light source. The illumination light output from the illumination light source passes through the positive lens and is projected onto the slit forming member.

The slit forming member passes part of the illumination light to generate slit light. The slit forming member of some typical examples has a pair of slit blades. The width of the region through which the illumination light passes is changed by changing the interval between the slit blades, thereby changing the width of the slit light. The region through which the illumination light passes is referred to as a slit, and the interval between the slit blades is referred to as a slit width. Further, the slit forming member may be configured to be capable of changing the length of the slit light. The length of the slit light is the size (dimension) of a cross section of the slit light along the direction perpendicular to the cross sectional width direction of the slit light that corresponds to the slit width. The width of the slit light and the length of the slit light of some typical examples are represented as the size of a projected image on the anterior segment formed by the slit light; however, possible representations of the width and length of the slit light are not limited to these. For example, the width and the length of the slit light may be represented as the sizes of the cross section of the slit light at a freely selected position, or as the sizes of the slit formed by the slit forming member.

The slit light generated by the slit forming member is refracted by the objective lens and is projected onto the anterior segment of the subject's eye E.

The illumination system 2 may further include a focus mechanism configured for changing the focal position of the slit light. The focus mechanism of some examples is configured to move the objective lens along the illumination optical axis 2a. The movement of the objective lens may be performed automatically and/or manually. Another focus mechanism may be configured to change the focal position of the slit light by: preparing and disposing a focusing lens at a position on the illumination optical axis 2a between the objective lens and the slit forming member; and moving the focusing lens along the illumination optical axis 2a.

FIG. 2 is a top view. As shown in FIG. 2, the direction along the axis of the subject's eye E is defined as the Z direction in the present aspect example. Of the directions perpendicular to the Z direction, the left-right direction (lateral direction) for the subject is defined as the X direction. The direction perpendicular to both the X direction and the Z direction is defined as the Y direction. In some typical examples, the X direction is parallel to the orientation of the line segment connecting the left and right eyes, and the Y direction is parallel to the orientation of the body axis of the subject.

The photography system 3 is configured to perform photography of the anterior eye segment while the slit light from the illumination system 2 is being projected onto the anterior eye segment. The reference character 3a denotes the optical axis of the photography system 3 (photography optical axis). The photography system 3 of the present aspect example includes the optical system 4 and the image sensor 5.

The optical system 4 is configured to direct light coming from the anterior segment of the subject's eye E onto which the slit light is being projected, to the image sensor 5. The image sensor 5 includes a light detecting plane that receives the light directed by the optical system 4.

The light directed by the optical system 4, that is, the light coming from the anterior segment of the subject's eye E, contains return light of the slit light being projected onto the anterior segment, and may further contain other kinds of light. Examples of the return light include reflected light, scattered light, and fluorescence induced by the slit light. Examples of the other kinds of light include light from the environment in which the slit lamp microscope 1 is installed, such as indoor light (room light) and sunlight. In the case where another illumination system different from the illumination system 2 is provided as an anterior segment illumination system for illuminating the entire anterior segment, return light of this anterior segment illumination light may be contained in the light directed by the optical system 4.

The image sensor 5 may be an area sensor that has a two dimensional image detecting area. The image sensor 5 of some examples may be a charge-coupled device (CCD) image sensor, a complementary metal oxide semiconductor (CMOS) image sensor, or an image sensor of another type.

The optical system 4 of some examples may have the same or similar configuration as or to photography systems of conventional slit lamp microscopes. For example, the optical system 4 includes an objective lens, a variable magnification optical system, and an imaging lens in the order from the side closer to the subject's eye E. The light coming from the anterior segment of the subject's eye E onto which the slit light is being projected, passes through the objective lens and the variable magnification optical system, and then forms an image on the light detecting plane of the image sensor 5 by the imaging lens.

The photography system 3 may further include a focus mechanism configured for changing the focal position of the photography system 3. The focus mechanism of some examples may be configured to move the objective lens along the photography optical axis 3a. The movement of the objective lens may be carried out automatically and/or manually. Note that a focusing lens may be prepared and disposed at a position in the photography optical axis 3a between the objective lens and the imaging lens, and focus mechanism may be capable of moving this focusing lens along the photography optical axis 3a, thereby changing the focal position of the photography system 3.

The illumination system 2 and the photography system 3 function as a Scheimpflug camera. More specifically, the illumination system 2 and the photography system 3 are configured in such a manner that the subject plane along the illumination optical axis 2a, the optical system 4, and the light detecting plane of the image sensor 5 satisfy what is commonly referred to as the Scheimpflug condition. More specifically, the YZ plane passing through the illumination optical axis 2a (the YZ plane contains the subject plane), the principal plane of the optical system 4, and the light detecting plane of the image sensor 5 intersect on the same straight line. As a result of such an arrangement, photographing can be performed with all positions in the subject plane in focus. In other words, photographing can be performed with all positions in the direction along the illumination optical axis 2a in focus.

The illumination system 2 and the photography system 3 of the present aspect example are configured in such a manner that at least an area defined by the anterior surface of the cornea C and the posterior surface of the crystalline lens CL is in focus of the photography system 3, for example. In other words, photography can be performed in a state in which the focus of the photography system 3 is on the entire area from the apex of the anterior surface of the cornea C ($Z=Z1$) to the apex of the posterior surface of the crystalline lens CL ($Z=Z2$) shown in FIG. 2. The location $Z=Z0$ corresponds to the Z coordinate of the intersection of the illumination optical axis 2a and the photography optical axis 3a. This enables observation over a wide area of the anterior eye segment and detection (diagnosis, examination, analysis, etc.) of various kinds of abnormalities in the anterior eye segment, including crystalline lens opacity caused by cataracts.

In some typical examples, the condition described above may be met by the configuration and arrangement of the elements included in the illumination system 2, the configuration and arrangement of the elements included in the photography system 3, and the relative position between the illumination system 2 and the photography system 3. A parameter indicating the relative position of the illumination system 2 and the photography system 3 may include the angle θ formed by the illumination optical axis 2a and the photography optical axis 3a, for example. The value of the angle θ may be set to 17.5 degrees, 30 degrees, or 45 degrees, for example. The angle θ may be variable.

The movement mechanism 6 is configured to move the illumination system 2 and the photography system 3. The movement mechanism 6 of some examples includes a movable stage, an actuator, and a mechanism. The illumination system 2 and the photography system 3 are fixed on the movable stage. The actuator is configured to operate based on a control signal input from the controller 7. The mechanism is configured to receive driving force generated by the actuator and move the movable stage. In some other examples, the movement mechanism 6 may include a movable stage on which the illumination system 2 and the photography system 3 are installed, and a mechanism configured to receive force applied to an operation device (not shown in the drawings) and move the movable stage. The operation device is a lever, for example. The movable stage may be movable at least in the X direction and may further be movable in at least one of the Y direction and the Z direction.

The movement mechanism 6 of the present aspect example is configured to integrally move the illumination system 2 and the photography system 3 in the X direction, for example. In other words, the movement mechanism 6 of the present aspect example is configured to move the illumination system 2 and the photography system 3 in the X direction while maintaining the state in which the above-mentioned Scheimpflug condition is satisfied. In parallel with this movement, the photography system 3 performs moving image photography with a predetermined time interval (photographing rate, acquisition rate), for example. As a result of this, a three dimensional area of the anterior segment of the subject's eye E is scanned with the slit light, and a plurality of images (an image group) corresponding to a plurality of cross sections in this three dimensional area is collected.

The controller 7 is configured to control each part of the slit lamp microscope 1. For example, the controller 7 controls elements of the illumination system 2 (e.g., illumination light source, slit forming member, focus mechanism, etc.), elements of the photography system 3 (e.g., focus mechanism, image sensor, etc.), the movement mechanism 6, the data processor 8, the output device 9, and other elements. Further, the controller 7 may be capable of executing control for changing the relative position of the illumination system 2 and the photography system 3.

The controller 7 includes a processor, a primary storage, a secondary storage, and the like. The secondary storage retains a control program. The control program may be stored in a computer or a storage to which the slit lamp microscope 1 can access. The functions of the controller 7 are implemented by cooperation of software such as the control program and hardware such as the processor.

The controller 7 is configured to be capable of executing the following controls on the illumination system 2, the photography system 3 and the movement mechanism 6 in order to apply scanning with slit light to a three dimensional area of the anterior segment of the subject's eye E.

Figure 3A:
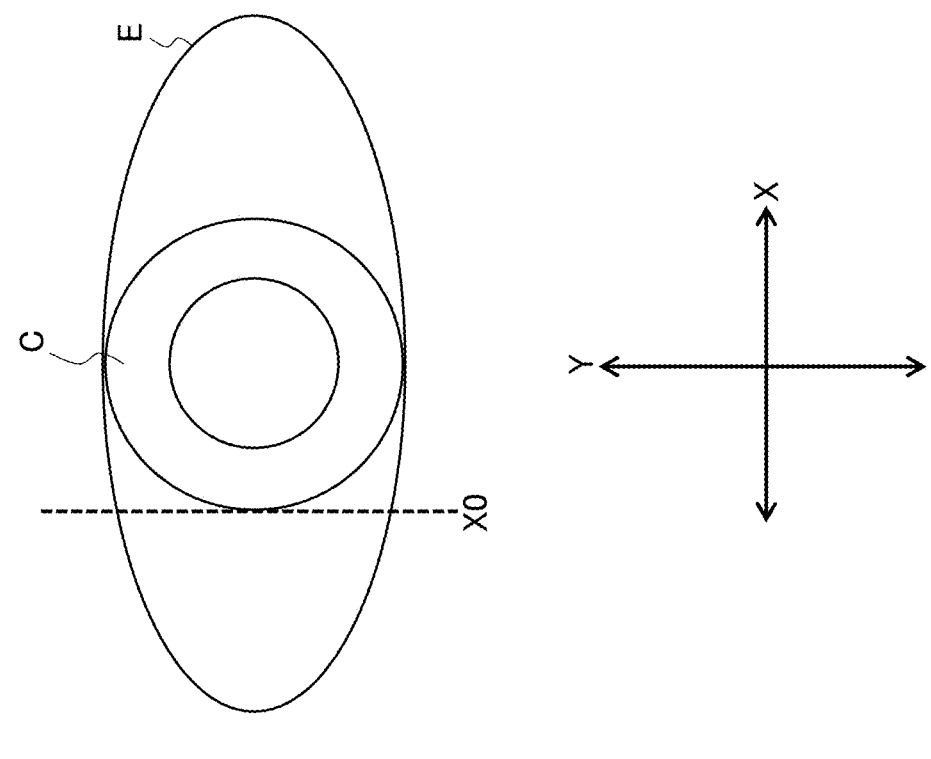
FIG. 3A is a schematic diagram for describing the operation of the medical system according to the aspect example.
Figure 3B:
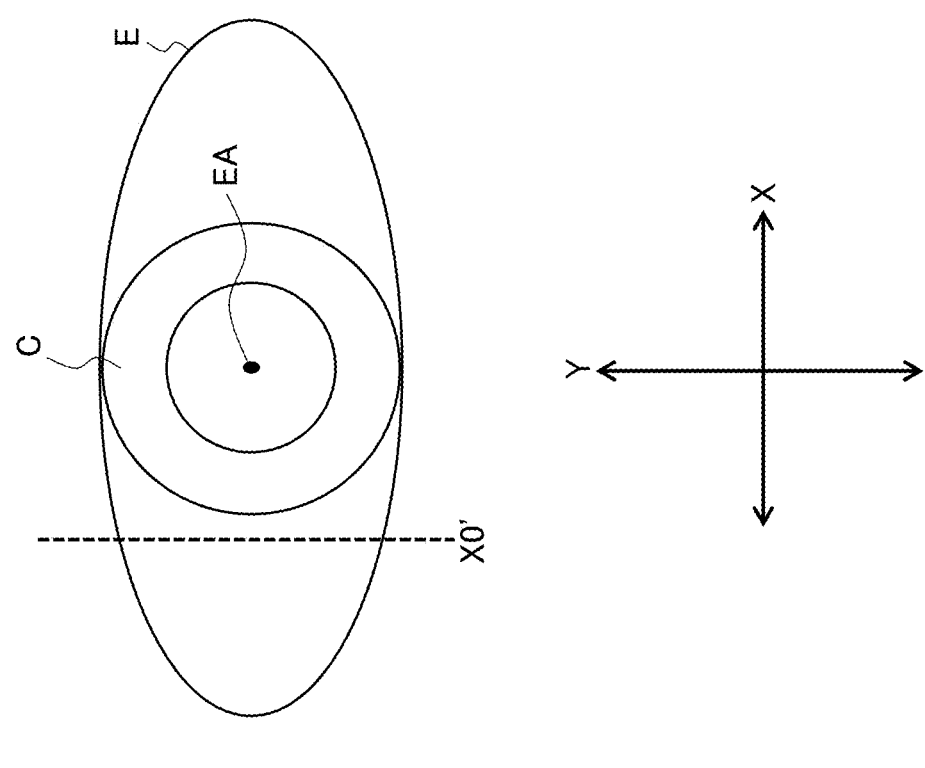
FIG. 3B is a schematic diagram for describing the operation of the medical system according to the aspect example.

First, the controller 7 controls the movement mechanism 6 to place the illumination system 2 and the photography system 3 at a predetermined scan start position. This control is referred to as alignment control. The scan start position is, for example, a position corresponding to the edge position (first edge position) of the cornea C in the X direction, or a position further away from the axis of the subject's eye E than the first edge position. The reference character X0 in FIG. 3A denotes an example of the scan start position corresponding to the first edge position of the cornea C in the X direction. Further, the reference character X0' in FIG. 38 denotes an example of the scan start position further away from the axis EA of the subject's eye E than the position corresponding to the first edge position of the cornea C in the X direction.

The controller 7 controls the illumination system 2 to start the projection of the slit light onto the anterior segment of subject's eye E. This control is referred to as slit light projection control. The slit light projection control may be performed before the execution of the alignment control or during the execution of the alignment control. The slit light is typically continuous light, but may be intermittent light (pulse light). The turning on/off control of the pulse light is synchronized with the photographing rate of the photography system 3. The slit light is typically visible light, but the slit light may be infrared light or a mixture of visible light and infrared light.

The controller 7 controls the photography system 3 to start moving image photography of the anterior segment of the subject's eye E. This control is referred to as photography control. The photography control may be performed before the execution of the alignment control or during the execution of the alignment control. In some typical examples, the photography control is executed simultaneously with the slit light projection control or after the slit light projection control.

After executing the alignment control, the slit light projection control, and the photography control, the controller 7 executes control of the movement mechanism 6 to start the movement of the illumination system 2 and the photography system 3. This control is referred to as movement control. The illumination system 2 and the photography system 3 are integrally moved by the movement control. In other words, the movement mechanism 6 moves the illumination system 2 and the photography system 3 while maintaining the relative position (e.g., the angle θ) between the illumination system 2 and the photography system 3. In some typical examples, the movement mechanism 6 moves the illumination system 2 and the photography system 3 while maintaining the state in which the aforementioned Scheimpflug condition is satisfied. The movement of the illumination system 2 and the photography system 3 is performed from the aforementioned scan start position to a predetermined scan end position. As in the scan start position, the scan end position is, for example, a position corresponding to the edge position (second edge position) of the cornea C on the opposite side of the first edge position in the X direction, or a position further away from the axis of the subject's eye E than the second edge position. With such movement control, the area from the scan start position to the scan end position becomes a scan area.

In some typical examples, the photography system 3 carries out the moving image photography in parallel with the projection of the slit light onto the anterior segment and the movement of the illumination system 2 and the photography system 3 in the X direction. Regarding this slit light, the width direction of the slit light corresponds to the X direction and the longitudinal direction of the slit light corresponds to the Y direction.

Here, the length of the slit light (that is, the size of the slit light in the Y direction) is set to be, for example, equal to or greater than the diameter of the cornea C on the surface of the subject's eye E. In other words, the length of the slit light is set to be equal to or greater than the corneal diameter in the Y direction. In addition, as described above, the distance of the movement of the illumination system 2 and the photography system 3 carried out by the movement mechanism 6 (that is, the scan area) is set to be equal to or greater than the corneal diameter in the X direction. Such design allows at least the entire cornea C to be scanned with the slit light.

With such scanning, a plurality of anterior segment images corresponding to mutually different slit light projection positions is acquired. In other words, such scanning yields a moving image that depicts the slit light moving in the X direction. An example of such a plurality of anterior segment images, that is, an example of a group of frames (a frame group) forming a moving image is illustrated in FIG. 4.

Figure 4:
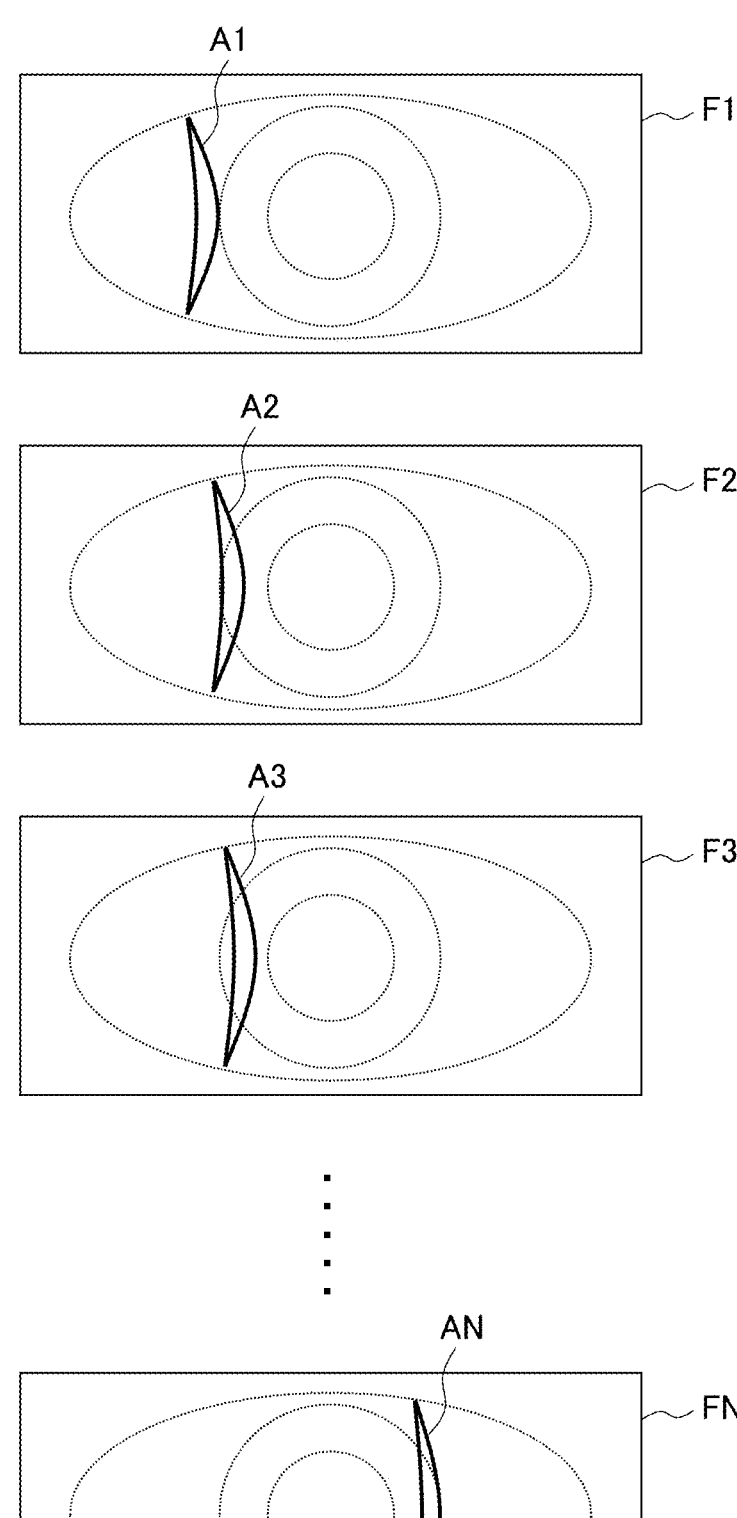
FIG. 4 is a schematic diagram for describing the operation of the medical system according to the aspect example.

FIG. 4 shows the plurality of anterior segment images (also called the frame group, or the image group) F1, F2, F3, . . . , and FN. The subscripts "n" of the anterior segment images Fn (n=1, 2, . . . , N) represent a time series order. In other words, the n-th anterior segment image acquired is represented by the reference character "Fn", The anterior segment image Fn includes the region An onto which the slit light is projected (slit light projected region An). As shown in FIG. 4, the positions of the slit light projected regions A1, A2, A3, . . . , and AN shift to the right in time series order. The scan start position and the scan end position in the example shown in FIG. 4 correspond to both edge positions of the cornea C in the X direction. Possible scan start positions and/or possible scan end positions are not limited to the present example. The scan start position and/or the scan end position may be a position(s) further away from the axis of the subject's eye E than the edge position(s) of the cornea, for example. In addition, the direction of scanning and the number of times of scans may be freely determined.

The data processor 8 executes various kinds of data processing. Data processed by the data processor 8 may be either any data acquired by the slit lamp microscope 1 or any data input from the outside. The data processor 8 can process images acquired by using the photography system 3. For example, various image correction processing, three dimensional image reconstruction, rendering, or the like can be applied to images acquired by the photography system 3.

The data processor 8 includes a processor, a primary storage, a secondary storage, and the like. The secondary storage retains a data processing program. The data processing program may be stored in a computer or a storage to which the slit lamp microscope 1 can access. The functions of the data processor 8 are implemented by cooperation of software such as the data processing program and hardware such as the processor.

The output device 9 outputs information from the slit lamp microscope 1. The output device 9 outputs images acquired by the slit lamp microscope 1 to the portable data storage 3000. For example, the slit lamp microscope 1 and the portable data storage 3000 conform to a predetermined serial bus standard and the output device 9 includes an interface conforming to this standard. The output device 9 may include a communication device configured to perform data communication between the slit lamp microscope 1 and other devices, a display device that displays information, a printer that records information on a printing medium, or other devices.

A description will be given of the alignment operation of the slit lamp microscope 1 with respect to the subject's eye E. In general, alignment is an operation of placing an optical system of an apparatus at an appropriate position for photography or measurement of a subject's eye. The alignment of the present aspect example is an operation of placing the illumination system 2 and the photography system 3 at appropriate positions for acquisition of a moving image as shown in FIG. 4.

There are various kinds of methods and techniques for alignment of ophthalmic apparatuses. While some examples of alignment methods and techniques will be described below, those applicable to the present aspect example are not limited to these examples.

One of the alignment methods and techniques applicable to the present aspect example is stereo alignment. The stereo alignment can be applied to an ophthalmic apparatus that can perform anterior eye segment photography from two or more mutually different directions (two or more mutually different viewpoints). An example method of the stereo alignment is disclosed by the present applicant in Japanese Unexamined Patent Application Publication No. 2013-248376. The stereo alignment of some examples includes the following steps: a step of photographing the anterior eye segment from different directions by two or more anterior segment cameras to acquire two or more photographed images; a step of analyzing these photographed images by a processor to determine a three dimensional position of the subject's eye; and a step of performing movement control of an optical system by a processor based on the three dimensional position determined. With this alignment operation, the optical system (the illumination system 2 and the photography system 3 in the present example) is brought to and placed at an appropriate alignment position with respect to the subject's eye. The stereo alignment of some typical examples uses the position of the pupil (e.g., the center of the pupil or the center of gravity of the pupil) of the subject's eye as a reference (or an indicator).

In addition to the stereo alignment described hereinbefore, any known alignment methods and techniques may be employed, such as an alignment method or technique using a Purkinje image formed by alignment light, an alignment method or technique using an optical lever, or an alignment method or technique using an alignment indicator. The alignment method or technique using a Purkinje image, an optical lever, or an alignment indicator uses the position of the corneal apex of the subject's eye as a reference.

Conventional, typical alignment methods and techniques including the above examples are performed for the purpose of matching the optical axis of an optical system with the axis of a subject's eye. Different from this, the present aspect example can perform alignment so as to place the illumination system 2 and the photography system 3 at a position corresponding to the scan start position.

The first example of the alignment of the present aspect example is operated to apply any of the alignment methods described above to perform alignment using the pupil or the corneal apex of the subject's eye E as a reference, and then move the illumination system 2 and the photography system 3 (in the X direction) by a distance corresponding to a preset standard value of corneal radius. This standard value may be replaced by a measurement value of the corneal radius of the subject's eye E.

The second example is operated to apply any of the alignment methods described above to perform alignment using the pupil or the corneal apex of the subject's eye E as a reference, execute analysis of an image of anterior segment of the subject's eye E to measure the corneal radius of the subject's eye E, and move the illumination system 2 and the photography system 3 (in the X direction) by a distance corresponding to the value obtained by this measurement. The image of the anterior segment analyzed in the present example is, for example, an anterior segment image obtained by the photography system 3 or another image. This another image may be an image of any kind, such as an image obtained by the anterior segment camera mentioned above, an image obtained by anterior segment OCT scanning, or the like.

The third example is operated to execute analysis of an image of the anterior segment acquired by the anterior segment camera for stereo alignment or by the photography system 3 to determine the first edge position of the cornea, and then move the illumination system 2 and the photography system 3 to a position corresponding to this first edge position by applying stereo alignment.

Note that the present aspect may be configured to perform any of the alignment methods described above to perform alignment using the pupil or corneal apex of the subject's eye E as a reference, and then commence anterior segment scanning with slit light from a position determined by this alignment. In this case as well, a scan sequence may be determined in such a manner that the entire cornea C is to be scanned. For example, the scan sequence may be determined in such a manner that scanning from the position determined by the alignment to the left and then to the right.

The slit lamp microscope 1 may be provided with a fixation system configured to output light (fixation light) for fixation of the subject's eye E. The fixation system of some typical examples includes at least one visible light source (fixation light source) or a display device that displays an image such as a landscape chart or a fixation target. The fixation system of some examples is arranged coaxially or non-coaxially with the illumination system 2 or the photography system 3. The fixation system may include an internal fixation system and/or an external fixation system. The internal fixation system is designed to present a fixation target to the subject through the optical path of an optical system of an apparatus. The external fixation system is designed to present a fixation target to the subject from a position outside the optical path of an optical system of an apparatus.

The kinds of images acquired by the slit lamp microscope 1 are not limited to an aforementioned moving image of an anterior eye segment (a plurality of anterior segment images). For example, the slit lamp microscope 1 may be able to acquire any of a three dimensional image constructed from a moving image, a rendered image constructed from the three dimensional image, a diaphanoscopic image (red reflex image). The three dimensional image of some examples may be either of the followings: stack data constructed by embedding, in the same three dimensional coordinate system, a plurality of anterior segment images respectively defined by different two dimensional coordinate systems; or volume data (voxel data) constructed by applying voxelization to stack data. The rendering of some examples is volume rendering, surface rendering, multiplanar reconstruction (MPR), or other rendering methods. The diaphanoscopic image is an image obtained using diaphanoscopy employed for depicting opacity and foreign bodies in an eye by using retinal reflection of illumination light. Note that the slit lamp microscope 1 may be capable of performing fundus photography, corneal endothelial cell photography, Meibomian gland photography, or other ophthalmic modalities.

Figure 5:
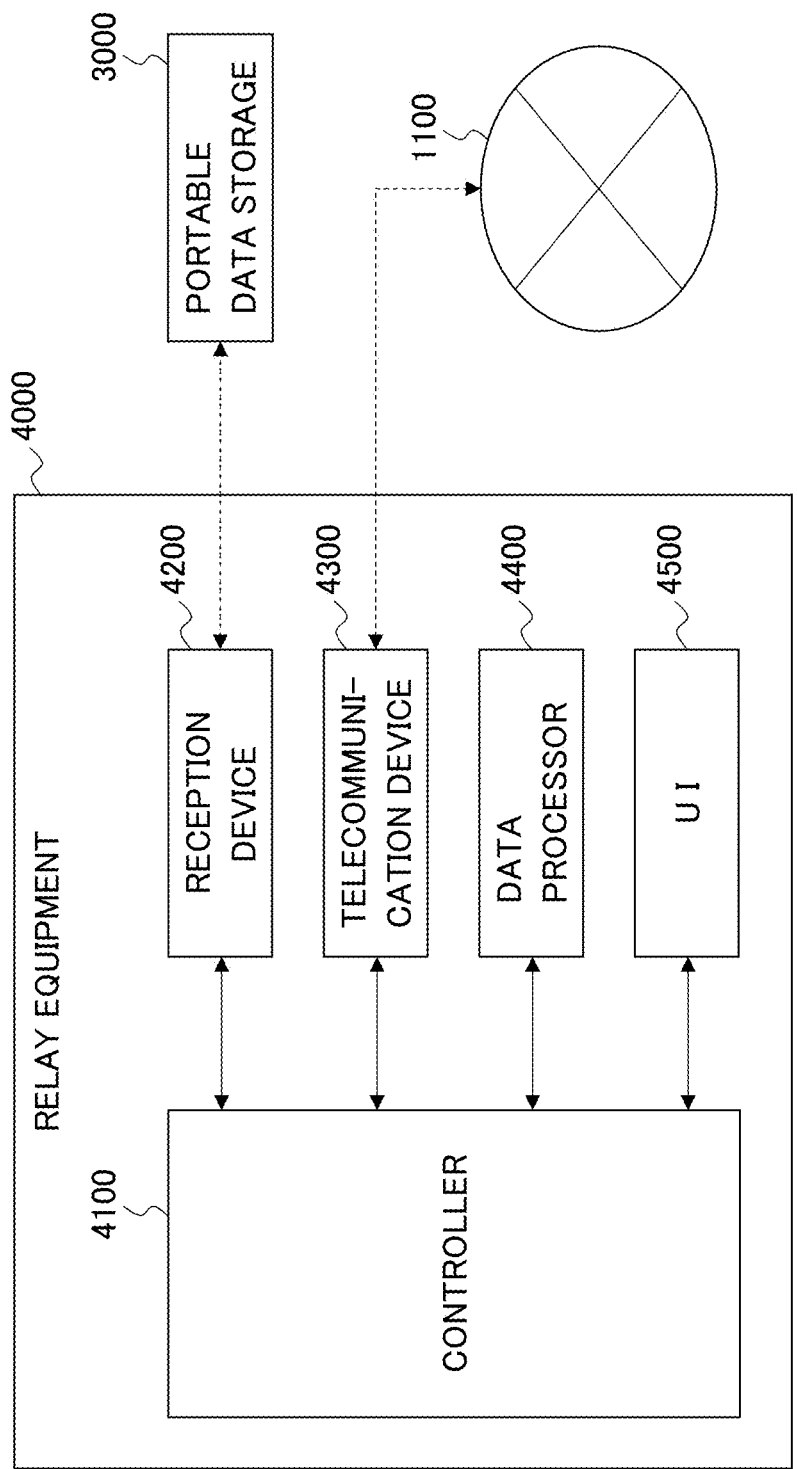
FIG. 5 is a schematic diagram illustrating the configuration of the medical system according to the aspect example.

The relay equipment 4000 is now described. An example of the configuration of relay equipment 4000 is shown in FIG. 5. The relay equipment 4000 in the present example includes the controller 4100, the reception device 4200, the telecommunication device 4300, the data processor 4400, and the user interface (UI) 4500.

The controller 4100 controls each part of the relay equipment 4000. The controller 4100 includes a processor, a primary storage, a secondary storage, and the like. The secondary storage retains a control program. The control program may be stored in a computer or a storage to which the relay equipment 4000 can access. The functions of the controller 4100 are implemented by cooperation of software such as the control program and hardware such as the processor.

The reception device 4200 receives information stored in the portable data storage 3000. The reception device 4200 of some examples includes at least one of an interface conforming to a predetermined serial bus standard and a drive device for reading information from a recording medium removed from the portable data storage 3000.

The telecommunication device 4300 includes a device configured for performing data communication via the telecommunication network 1100.

The data processor 4400 performs various data processing. The data processor 4400 includes a processor, a primary storage, a secondary storage, and the like. The secondary storage retains a data processing program. The data processing program may be stored in a computer or a storage to which the relay equipment 4000 can access. The functions of the data processor 4400 are implemented by cooperation of software such as the data processing program and hardware such as the processor.

The user interface 4500 includes a display device, an operation device, and the like.

Some examples of processes that can be performed by the relay equipment 4000 and some examples of processes that can be performed by the elements of the relay equipment 4000 will be described later.

Figure 6:
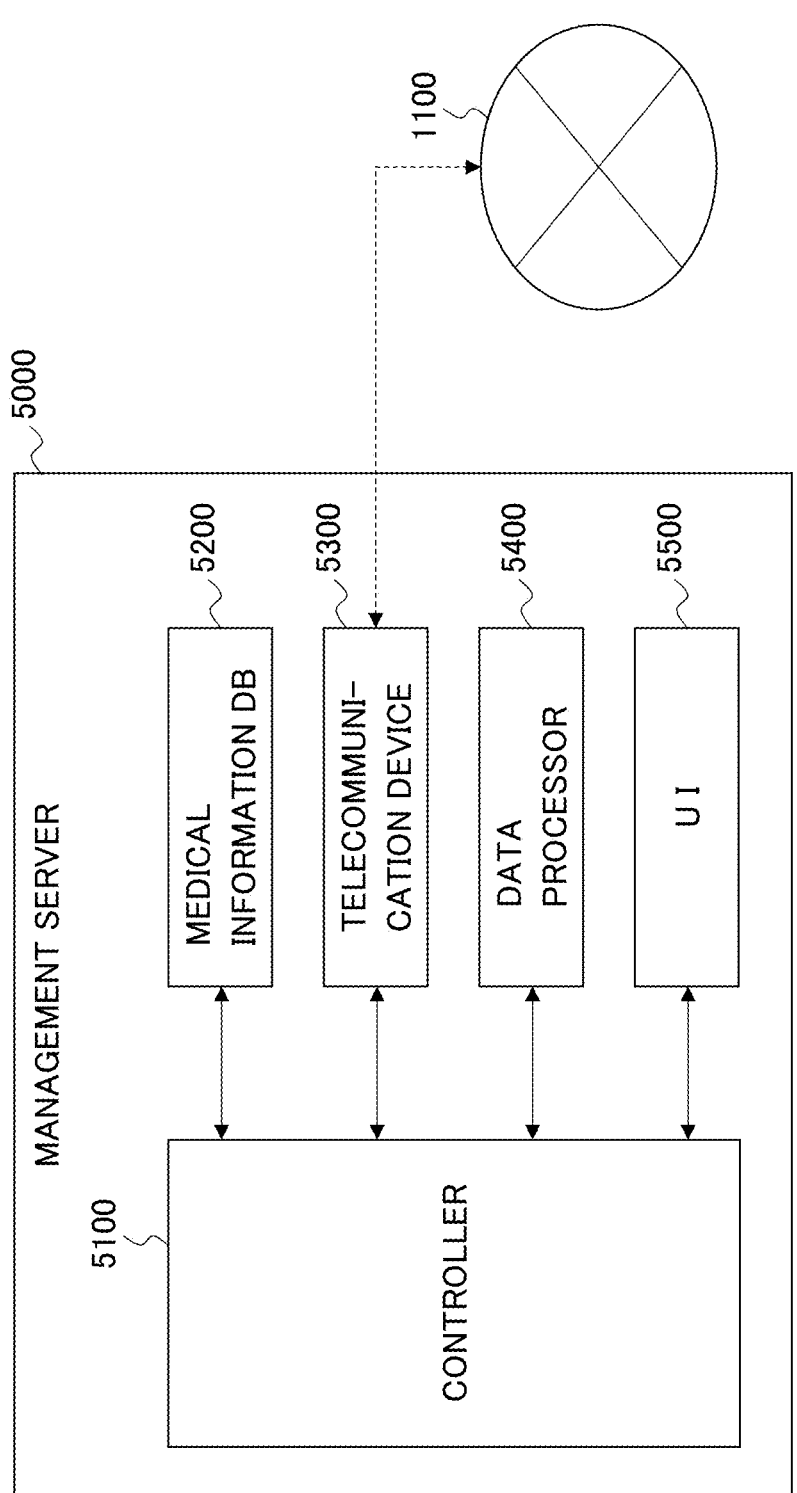
FIG. 6 is a schematic diagram illustrating the configuration of the medical system according to the aspect example.

The management server 5000 is now described. An example of the configuration of the management server 5000 is shown in FIG. 6. The management server 5000 in the present example includes the controller 5100, the medical information database (medical information DB) 5200, the telecommunication device 5300, the data processor 5400, and the user interface (UI) 5500.

The controller 5100 controls each part of the management server 5000. The controller 5100 includes a processor, a primary storage, a secondary storage, and the like. The secondary storage retains a control program. The control program may be stored in a computer or a storage to which the management server 5000 can access. The functions of the controller 5100 are implemented by cooperation of software such as the control program and hardware such as the processor.

The medical information database 5200 manages various kinds of medical information. In some typical examples, the medical information is managed for individual subjects. Identification of individual subjects is performed, for example, using identifiers (subject IDs) assigned to individual subjects. The generation and assignment of the subject IDs in some examples are executed by the management server 5000 (e.g., the data processor 5400).

In some typical examples, the medical information managed by the medical information database 5200 includes at least authentication information for individual subjects to whom medical examinations have been conducted in on-site examinations and examination data obtained from individual subjects by the medical examinations. In addition, the medical information managed by the medical information database 5200 may further include examination history for individual subjects to which subject IDs are respectively assigned.

In the present example, authentication information is typically biometric authentication information (biometrics information), examination data is typically anterior segment images acquired by the slit lamp microscope 1, and examination history is typically examination date information. The examination date information may be a piece of information showing a specific date (and time) corresponding to an examination applied to a corresponding subject. For example, the examination date information may be information showing any of the followings: the date of performing a corresponding examination; the date of reading out of corresponding information from the portable data storage 3000; the date of transmitting corresponding information from the relay equipment 4000 to the management server 5000; and the date of receiving corresponding information from the relay equipment 4000 by the management server 5000.

The medical information database 5200 includes a processor, a primary storage, a secondary storage, and a large capacity storage (mass storage), and the like. The secondary storage retains a database management program. The functions of the medical information database 5200 are implemented by cooperation of software such as the database management program and hardware such as the processor.

The telecommunication device 5300 includes a device configured for performing data communication via the telecommunication network 1100.

The data processor 5400 performs various data processing. The data processor 5400 includes a processor, a primary storage, a secondary storage, and the like. The secondary storage retains a data processing program. The functions of the data processor 5400 are implemented by cooperation of software such as the data processing program and hardware such as the processor.

The user interface 5500 includes a display device, an operation device, and the like.

Some examples of processes that can be performed by the management server 5000 and some examples of processes that can be performed by the elements of the management server 5000 will be described later.

Figure 7A:
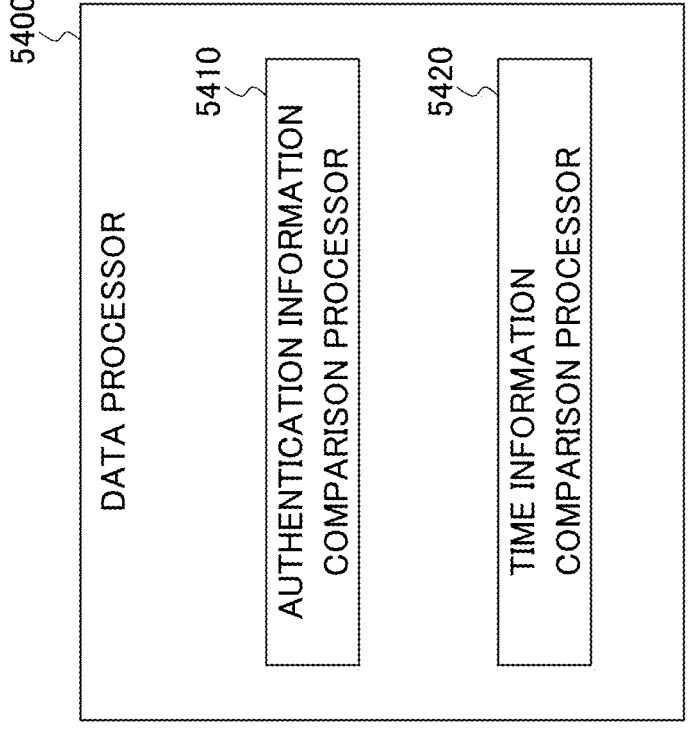
FIG. 7A is a schematic diagram illustrating the configuration of the medical system according to the aspect example.
Figure 7B:
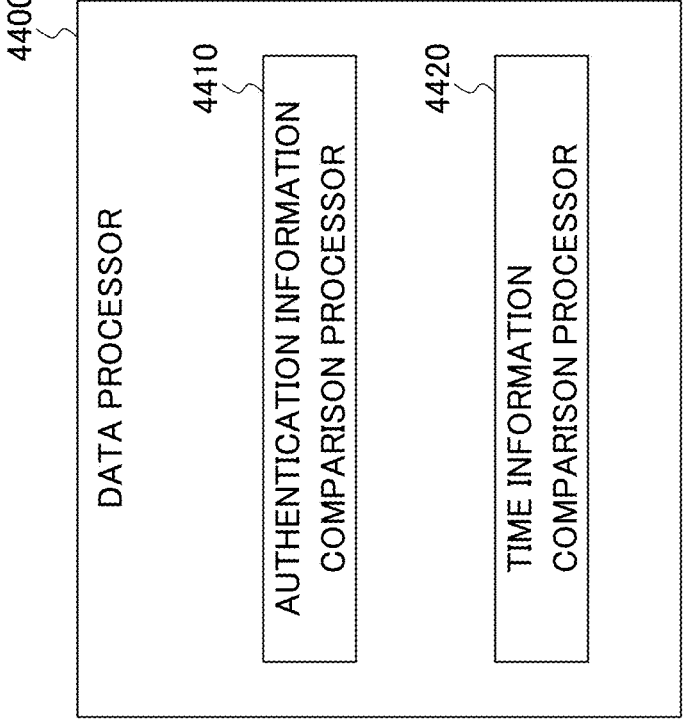
FIG. 7B is a schematic diagram illustrating the configuration of the medical system according to the aspect example.

The medical system 1000 may be configured to perform comparison processing (check processing, identification processing) for preventing omissions and duplication of examination data. Some examples of a configuration for this purpose are described now. FIG. 7A shows an example of a configuration in which the management server 5000 has a comparison function, and FIG. 7B shows an example of a configuration in which the relay equipment 4000 has a comparison function. The medical system 1000 of some examples may include any of: at least part of the configuration example in FIG. 7A; at least part of the configuration example in FIG. 7B; and a combination of at least part of the configuration example of FIG. 7A and at least part of the configuration example of FIG. 7B.

FIG. 7A shows an example of the configuration of the data processor 5400 of the management server 5000. The data processor 5400 of the present example includes the authentication information comparison processor 5410 and the time information comparison processor 5420.

The authentication information comparison processor 5410 is configured to compare authentication information sent from the relay equipment 4000 with the medical information database 5200. More specifically, when receiving authentication information of a subject sent from the relay equipment 4000, the authentication information comparison processor 5410 compares this authentication information with authentication information of this subject stored in the medical information database 5200. In the case where authentication information is biometric authentication information, the authentication information comparison processor 5410 determines whether the biometric authentication information sent from the relay equipment 4000 and the biometric authentication information of this subject stored in the medical information database 5200 both belong to (correspond to) the same person. The biometric authentication technique applicable to this example may be any known technique, such as iris authentication, fingerprint authentication, face authentication, palm authentication, retina authentication, blood vessel authentication, voice authentication, ear shape authentication, handwriting authentication, lip movement authentication, blink authentication, gait authentication, or other authentication techniques.

The time information comparison processor 5420 is configured to compare time information sent from the relay equipment 4000 with the medical information database 5200. More concretely, when receiving time information on an examination of a subject sent from the relay equipment 4000, the time information comparison processor 5420 compares this time information with examination history of this subject stored in the medical information database 5200. The definition of time information may be the same as or different from the definition of examination date information recorded in examination history. Time information may be a specific date (and time) corresponding to an examination applied to a subject, such as the date of performing an examination, the date of reading out information from the portable data storage 3000, the date of transmitting information from the relay equipment 4000 to the management server 5000, and the date of receiving information from the relay equipment 4000 by the management server 5000. In some examples, the time information comparison processor 5420 may be configured to determine whether the same examination date as the date indicated by the time information is recorded in the examination history. In some other examples, the time information comparison processor 5420 may be configured to determine whether any of examination dates recorded in the examination history belong to a specific period of time that has been set based on the date indicated by the time information. This specific period of time may be freely set. In some other examples, the time information comparison processor 5420 may be configured to determine whether the date indicated by the authentication information belongs to a specific period of time that has been set based on one or more of the examination dates recorded in the examination history. The setting method of this specific period of time may be optional.

FIG. 7B shows an example of the configuration of the data processor 4400 of the relay equipment 4000. The data processor 4400 in the present example includes the authentication information comparison processor 4410 and the time information comparison processor 4420.

The authentication information comparison processor 4410 of some examples is configured to compare authentication information sent from the management server 5000 with authentication information stored in the portable data storage 3000. The technique of this comparison performed by the authentication information comparison processor 4410 may be the same as that performed by the authentication information comparison processor 5410.

The time information comparison processor 4420 of some examples is configured to compare time information sent from the management server 5000 with time information stored in the portable data storage 3000. The technique of this comparison performed by the time information comparison processor 4420 may be the same as that performed by the time information comparison processor 5420.

In the case where medical information includes time information, the medical system 1000 may include an element configured to generate time information. This element, a time information generation processor, is configured to generate time information corresponding to a medical examination applied to a subject. Some examples of the time information generation processor are now described with reference to FIG. 8A to FIG. 8E. At least one of these examples may be applied to the medical system 1000.

In the case where two or more examples of the time information generation processor are employed, the two or more time information generation processors can be operated selectively or in parallel. For example, when a first time information generation processor generates time information at a stage of a series of processes performed by the medical system 1000, a second time information generation processor arranged at a stage more downstream than the first time information generation processor, does not execute generation of time information. In other words, a time information generation processor may be configured to generate time information only when no time information is attached to examination data. In some other examples, all of a plurality of time information generation processors may respectively generate a plurality of pieces of time information for the same examination data and attach them to this examination data.

Figure 8A:
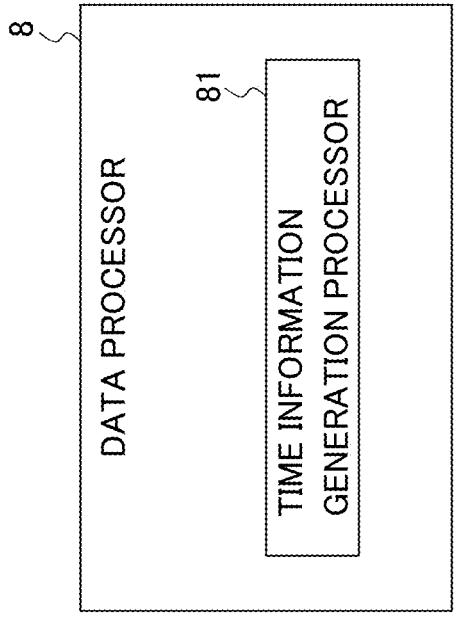
FIG. 8A is a schematic diagram illustrating the configuration of the medical system according to the aspect example.

FIG. 8A shows an example of the configuration in the case where the time information generation processor is included in the slit lamp microscope 1 (the medical examination apparatus 2000). The data processor 8 of the present example includes the time information generation processor 81. The time information generation processor 81 is configured to generate the date of performing a medical examination on a subject as time information corresponding to this medical examination performed on this subject.

The time information generation processor 81 of some typical examples includes a timer. The timer of some examples measures the elapsed time from a certain time point. The time information generation processor 81 may be configured to provide a date and/or time at any time point by using a date and/or time at the start of a measurement as a reference. In some typical examples, a reference date and/or a reference time are/is set when the slit lamp microscope 1 is situated in an available area of the telecommunication network 1100, and measurements are commenced.

In an examination of an eye, a control signal from the controller 7 (for example, a control signal corresponding to the aforementioned photography control) is input to the time information generation processor 81. The time information generation processor 81 may be configured to generate time information by obtaining the date and/or time at the time point when this control signal is received from the timer. The generated time information is associated with examination data acquired by the examination of the eye. Medical information including the time information and the examination data is transmitted to and saved in the portable data storage 3000.

Figure 8B:
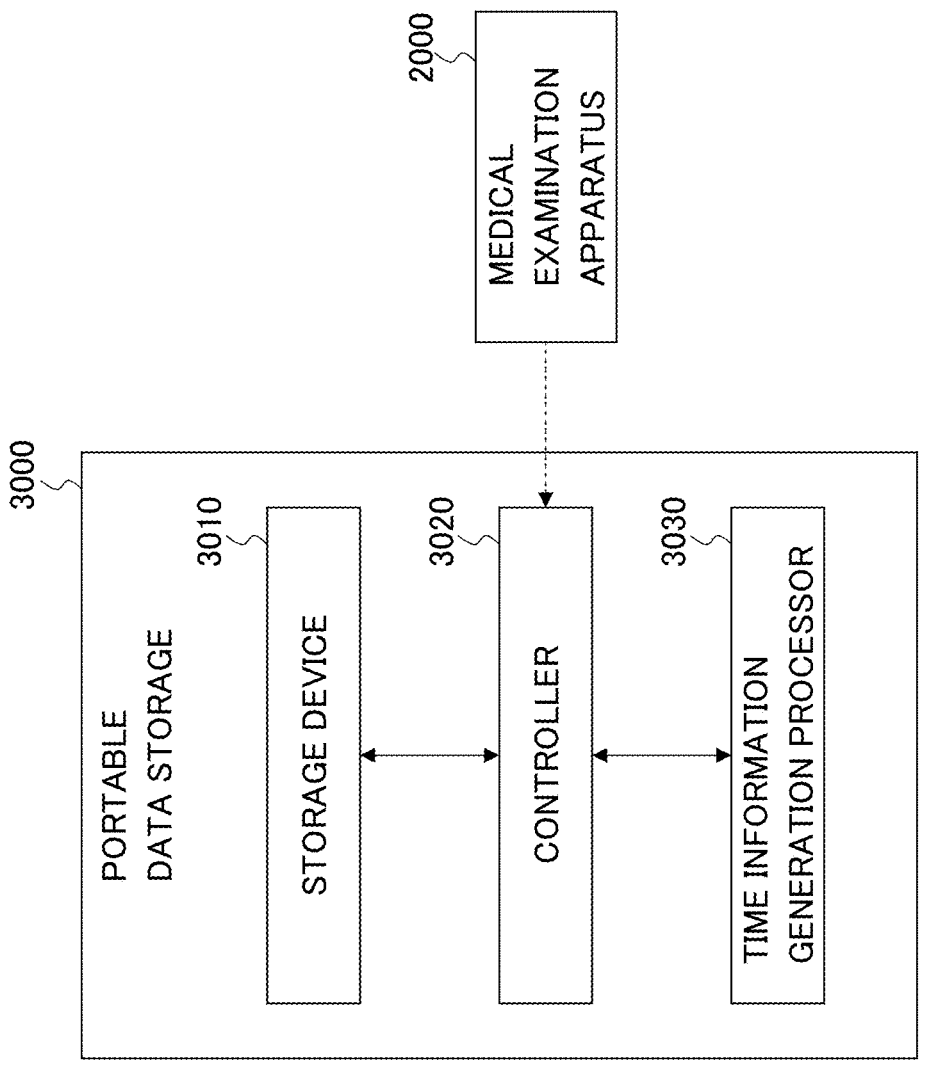
FIG. 8B is a schematic diagram illustrating the configuration of the medical system according to the aspect example.

FIG. 8B shows an example of the case where the time information generation processor is arranged in the portable data storage 3000. The portable data storage 3000 of the present example includes the storage device 3010, the controller 3020, and the time information generation processor 3030. Various kinds of data are stored in the storage device 3010. The storage device 3010 of some typical examples includes a large capacity storage.

The controller 3020 controls each part of the portable data storage 3000. The controller 3020 includes a processor, a primary storage, a secondary storage, and the like. The secondary storage retains a control program. The functions of the controller 3020 are implemented by cooperation of software such as the control program and hardware such as the processor.

The time information generation processor 3030 generates, as time information corresponding to a medical examination performed on a subject, the date of conducting the medical examination on the subject. The time information generation processor 3030 may have the same or similar functions and configuration as or to the time information generation processor 81 of FIG. 8A.

In an eye examination, examination data is input from the medical examination apparatus 2000 (the slit lamp microscope 1) to the portable data storage 3000. The controller 3020 notifies the time information generation processor 3030 of the fact that the examination data has been input. The time information generation processor 3030 may be configured to generate time information by obtaining, from a timer, the date and/or time at the time point of receiving this notification. The generated time information is sent to the controller 3020. The controller 3020 associates the time information input from the time information generation processor 3030 with the examination data input from the medical examination apparatus 2000. The controller 3020 stores medical information including the time information and the examination data in the storage device 3010.

Figure 8C:
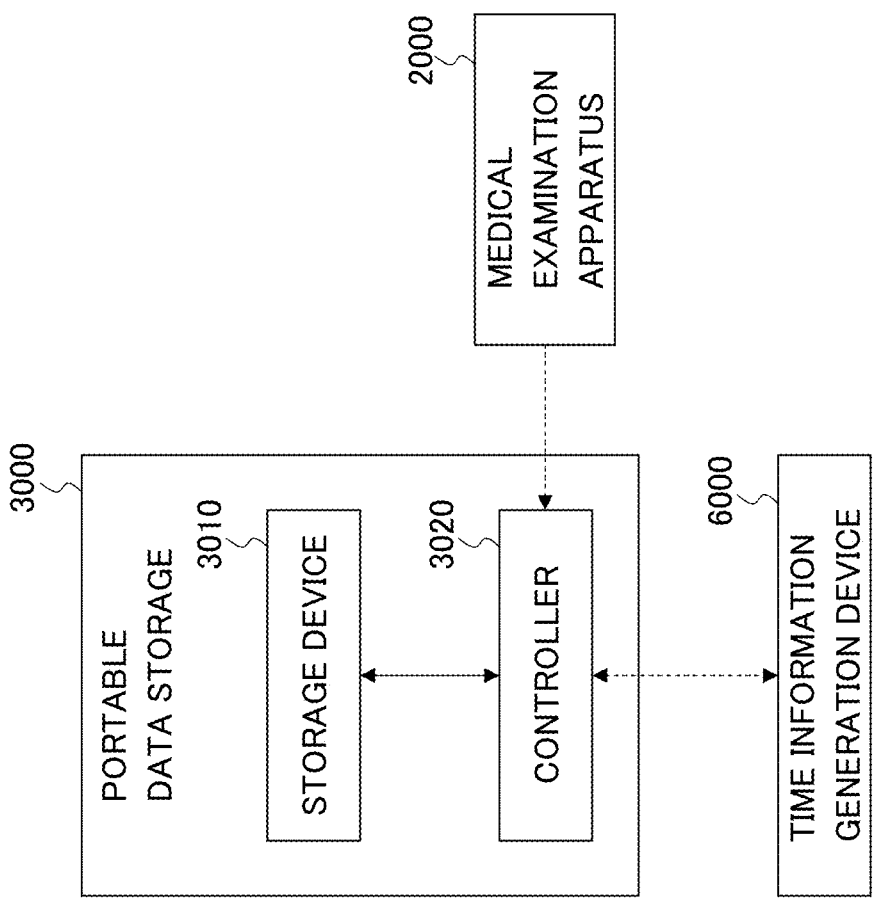
FIG. 8C is a schematic diagram illustrating the configuration of the medical system according to the aspect example.

FIG. 8C shows an example of a time information generation device that is carried with the portable data storage 3000. The portable data storage 3000 of the present example includes the storage device 3010 and the controller 3020. These elements may have the same functions and configuration as those shown in FIG. 8B.

The time information generation device 6000 generates, as time information corresponding to a medical examination performed on a subject, the date of conducting the medical examination on the subject. The time information generation processor 3030 may have the same or similar functions and configuration as or to the time information generation processor 81 of FIG. 8A.

In an eye examination, examination data is input from the medical examination apparatus 2000 (the slit lamp microscope 1) into the portable data storage 3000, and then the controller 3020 executes control of notifying the time information generation device 6000 of the fact that the examination data has been input. The time information generation device 6000 may be configured to generate time information by obtaining, from a timer, the date and/or time at the time point of receiving this notification. The generated time information is sent to the controller 3020. The controller

3020 associates the time information input from the time information generation device 6000 with the examination data input from the medical examination apparatus 2000. The controller 3020 stores medical information including the time information and the examination data in the storage device 3010.

Figure 8D:
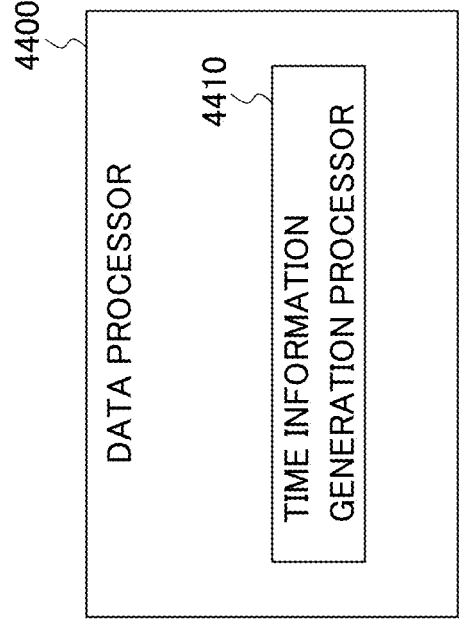
FIG. 8D is a schematic diagram illustrating the configuration of the medical system according to the aspect example.

FIG. 8D shows an example of the case where the time information generation processor is arranged in the relay equipment 4000. The data processor 4400 of the present example includes the time information generation processor 4410. The time information generation processor 4410 generates, as time information corresponding to a medical examination performed on a subject, the date and/or time of reading out at least part of the medical information from the portable data storage 3000. The time information generation processor 4410 may have the same or similar functions and configuration as or to the time information generation processor 81 in FIG. 8A. As in the example shown in FIG. 8C, a time information generation device may be provided as a peripheral device of the relay equipment 4000.

Before, during, or after reading out information from the portable data storage 3000, the controller 4100 of the relay equipment 4000 obtains the current date and/or time from time information generation processor 4410. For example, the controller 4100 sends a reading-out control signal to the reception device 4200 and obtains the current date and/or time from the time information generation processor 4410. The controller 4100 associates the time information input from the time information generation processor 4410 with the information read out from the portable data storage 3000 by the reception device 4200.

The relay equipment 4000 may be configured to transmit medical information including these pieces of information to the management server 5000. If this is the case, the time information generation processor 4410 generates, as time information corresponding to the medical examination performed on the subject, the date on which the relay equipment 4000 transmits at least part of the medical information to the management server 5000.

Figure 8E:
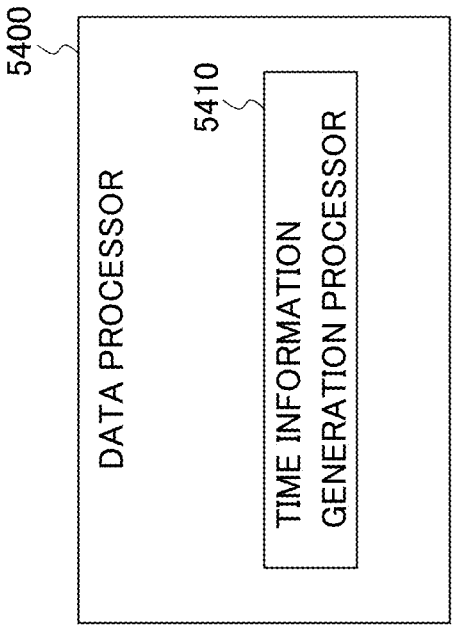
FIG. 8E is a schematic diagram illustrating the configuration of the medical system according to the aspect example.

FIG. 8E shows an example of the case where the time information generation processor is arranged in the management server 5000. The data processor 5400 of the present example includes the time information generation processor 5410. The time information generation processor 5410 generates, as time information corresponding to a medical examination performed on a subject, the date and/or time on which the relay equipment 4000 transmits at least part of the medical information to the management server 5000. In other words, the time information generation processor 5410 generates the date and/or time on which the management server 5000 receives the information sent from the relay equipment 4000. As in the example shown in FIG. 8C, a time information generation device may be provided as a peripheral device of the management server 5000.

The telecommunication device 5300 receives the information sent from the relay equipment 4000, and then the controller 5100 obtains the current date and/or time from the time information generation processor 5410. The controller 5410 associates the time information input from the time information generation processor 5410 with the information received by the telecommunication device 5300. The controller 5100 may store medical information including these pieces of information in the medical information database 5200.

As mentioned above, medical information includes authentication information. The medical system 1000 may include an element configured to generate authentication information. This element, an authentication information generation processor, is configured to generate authentication information corresponding to a medical examination performed on a subject. The generated authentication information is associated with examination data. The medical information of the present aspect example includes at least the authentication information and the examination data, and may further include time information described above.

Some examples of the authentication information generation processor are now described with reference to FIG. 9A and FIG. 9B. At least one of these examples may be applied to the medical system 1000.

Figure 9A:
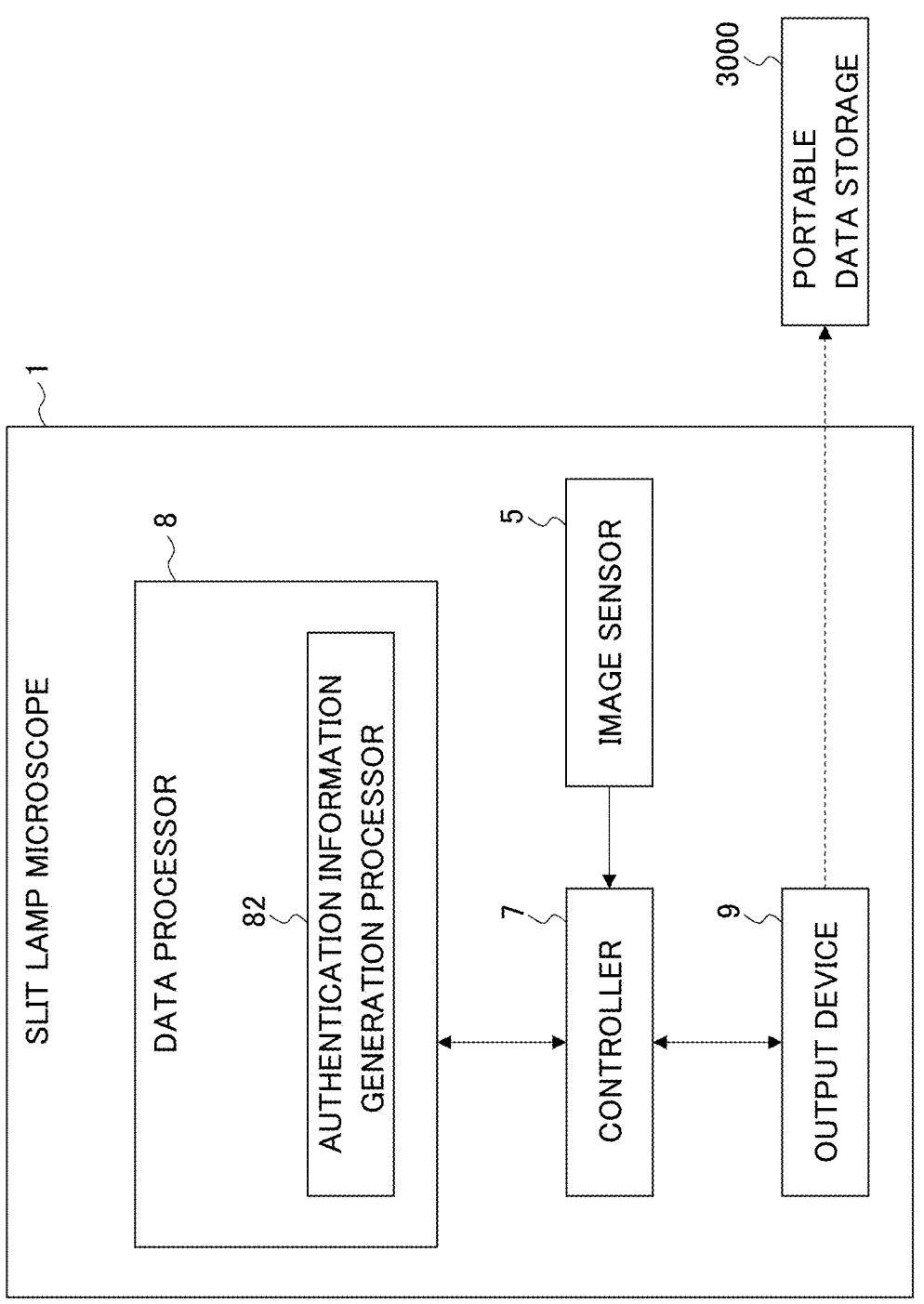
FIG. 9A is a schematic diagram illustrating the configuration of the medical system according to the aspect example.

FIG. 9A shows an example of the case where the authentication information generation processor is arranged in the slit lamp microscope 1 (the medical examination apparatus 2000). The data processor 8 of the present example includes the authentication information generation processor 82.

The authentication information generation processor 82 of some typical examples generates biometric authentication information (biometrics information). For example, the slit lamp microscope 1 generates authentication information that includes an anterior segment image acquired by the image sensor 5. This authentication information may be one or more anterior segment images. This anterior segment image (s) may or may not include a projected image of slit light. In other words, this anterior segment image(s) may be acquired either when slit light is or is not being projected. In some examples of the former case, the authentication information generation processor 82 may be configured to obtain, as authentication information, one or more images of an image group collected by anterior segment scanning using slit light. In some examples of the latter case, the slit lamp microscope 1 may perform anterior segment photography separately from anterior segment scanning with slit light, and use an anterior segment image acquired by this anterior segment photography as authentication information. An anterior segment image as authentication information may be used for iris authentication, blood vessel authentication, or the like.

The controller 7 transmits medical information including at least authentication information and examination data, to the output device 9. The output device 9 transmits this medical information to the portable data storage 3000 under control of the controller 7.

Figure 9B:
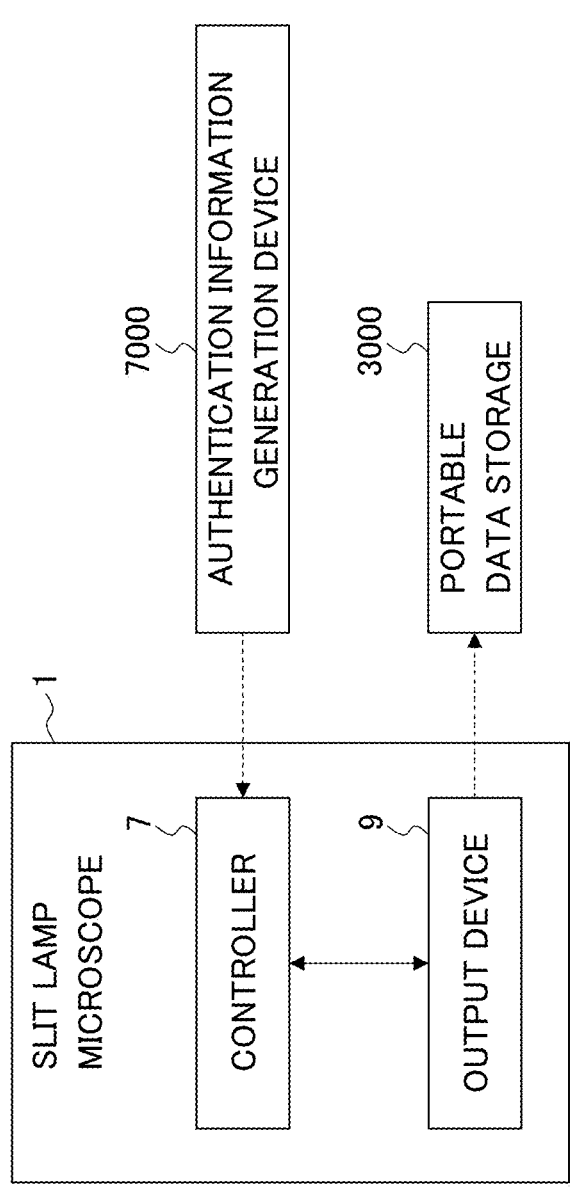
FIG. 9B is a schematic diagram illustrating the configuration of the medical system according to the aspect example.

FIG. 9B shows an example of an authentication information generation device used together with the medical examination apparatus 2000 (the slit lamp microscope 1) and the portable data storage 3000. The authentication information generation device 7000 of some typical examples generates biometric authentication information (biometrics information).

The authentication information generation device 7000 of some examples may include one or more of the following devices: a camera configured to acquire an iris image (anterior segment image) for iris authentication; a fingerprint scanner configured to perform scanning of a fingertip for fingerprint authentication; a camera configured to acquire a face image for face authentication; a palm scanner configured to perform scanning of a palm for palm authentication; a camera configured to acquire a retinal image for retina authentication; a device configured to perform photography or scanning of a predetermined body part for blood vessel authentication; a recorder configured to record sound (voice) for voice authentication; a camera configured to acquire an ear image for ear shape authentication; a device configured to record handwriting for handwriting authentication; a camera configured to acquire a video (moving image) of lips when speaking for lip movement authentication; a camera configured to acquire a video of an eye for blink authentication; and a camera configured to acquire a video of a body for gait authentication.

The controller 7 sends medical information including at least authentication information generated for a subject and examination data obtained from this subject, to the output device 9. The output device 9 sends this medical information to the portable data storage 3000 under control of the controller 7.

Some examples of the operations of the medical system 1000 are now described.

FIG. 10A to FIG. 10E illustrate the first example of the operation of the medical system 1000.

In some examples, an examiner(s) travels to an on-site examination site by a vehicle on which the medical examination apparatus 2000 (the slit lamp microscope 1) and the portable data storage 3000 are loaded. The examiner may also carry the time information generation device 6000 and/or the authentication information generation device 7000. A reference date and/or a reference time may be set during the time information generation device 6000 is within an available area of the telecommunication network 1100.

Figure 10A:
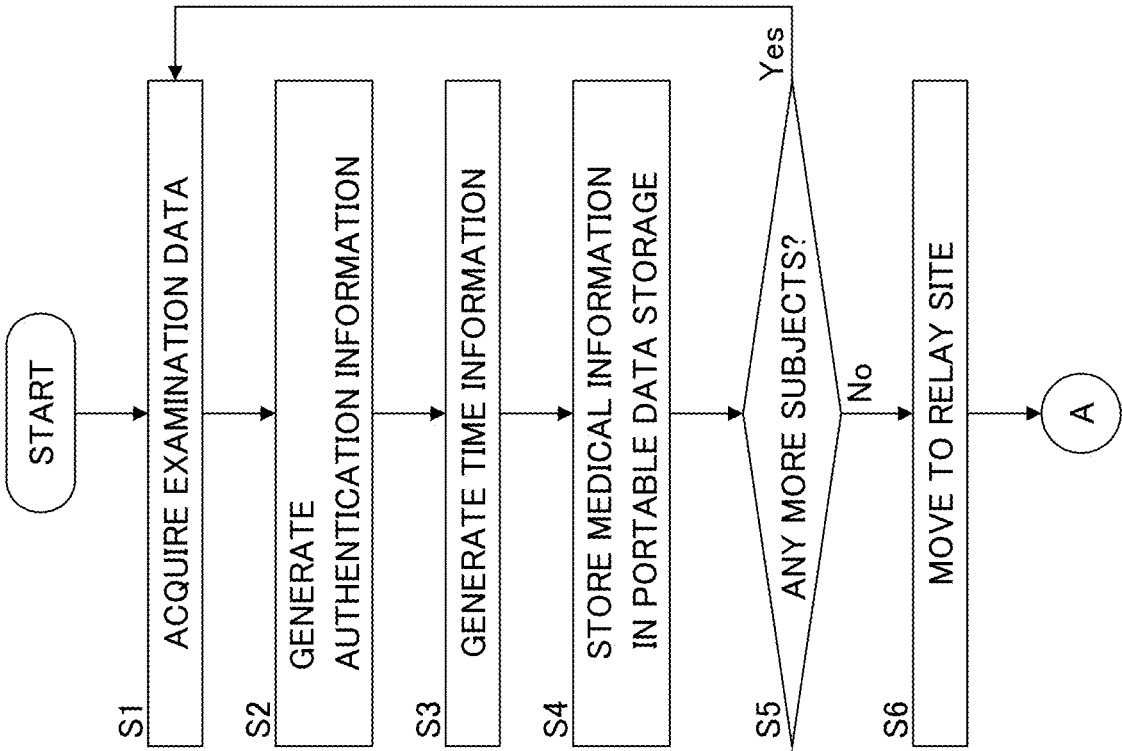
FIG. 10A is a flowchart illustrating the operation of the medical system according to the aspect example.

FIG. 10A is now referred to. At the on-site examination site, the examiner conducts examinations on subjects using the medical examination apparatus 2000, thereby acquiring examination data for individual subjects (S1). In addition, generation of authentication information (S2) and generation of time information (S3) are performed for individual subjects. The timings and the order of the examination data acquisition, the authentication information generation, and the time information generation may be freely determined.

The medical examination apparatus 2000 or the portable data storage 3000 can manage examination data, authentication information, and time information for a subject as medical information for this subject. For example, the medical examination apparatus 2000 or the portable data storage 3000 creates medical information files for individual subjects and stores examination data, authentication information and time information for a subject in the medical information file for this subject. The medical information of each subject obtained in this way is stored in the portable data storage 3000 (S4).

The steps S1 to S4 are repeated until medical information is obtained for all subjects at the on-site examination site (S5: Yes). After medical information for all of the subjects has been obtained (S5: No), the examiner puts the medical examination apparatus 2000, the portable data storage 3000, etc. into the vehicle and travels to a relay site (S6). The relay site is a place from which the medical information stored in the portable data storage 3000 is transmitted to the management server 5000. The relay site of the present aspect example may be a facility where the relay equipment 4000 is installed. The examiner may come to the relay site via other one or more on-site examination sites. In this case, the processes of the steps S1 to S5 are performed also at each of the one or more on-site examination sites.

Figure 10B:
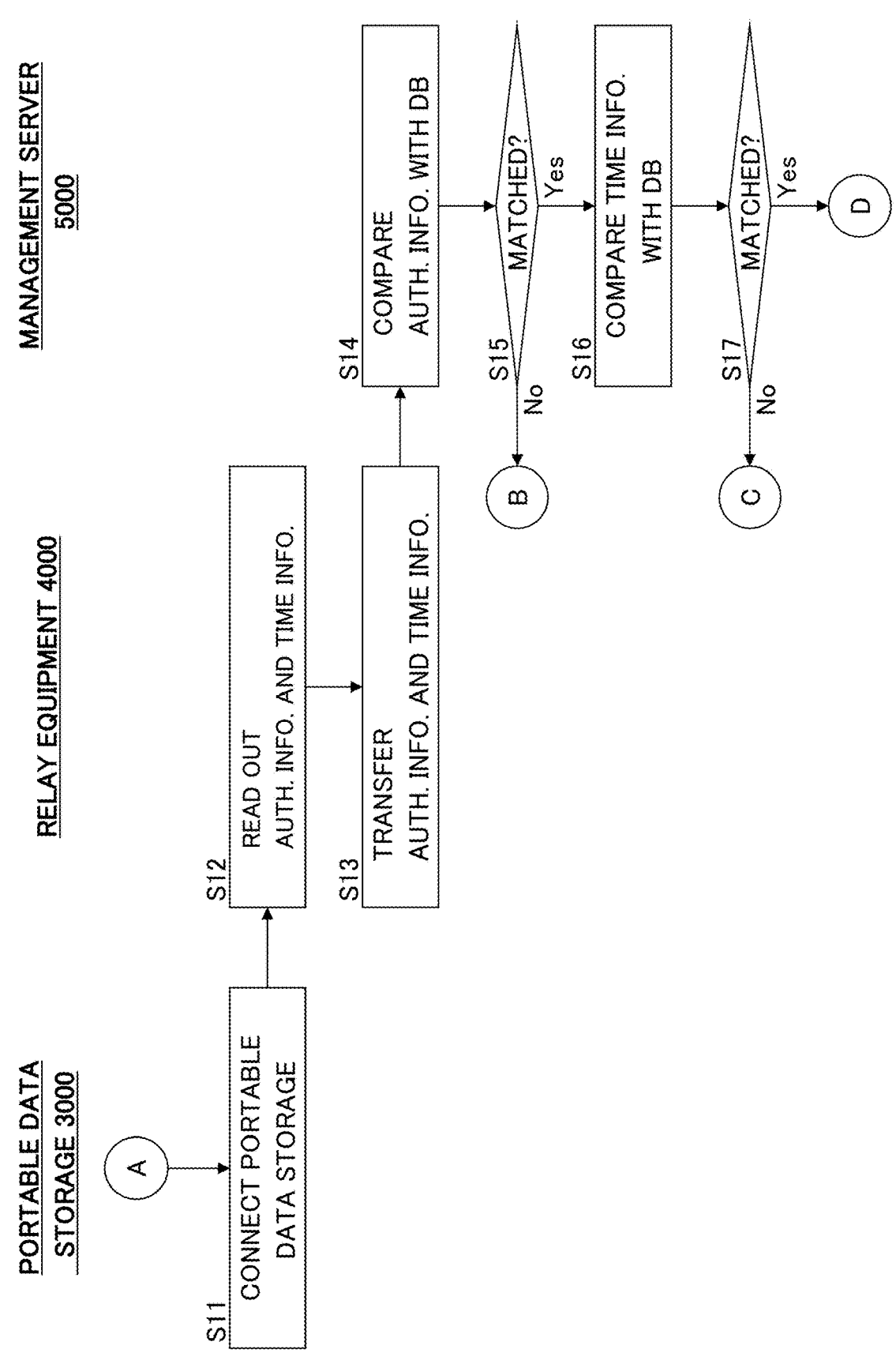
FIG. 10B is a flowchart illustrating the operation of the medical system according to the aspect example.

FIG. 10B is then referred to. After the portable data storage 3000, which stores the medical information collected at the on-site examination site(s), the portable data storage 3000 is connected to the relay equipment 4000 (S11). As mentioned above, the aspect of this connection is optional.

The relay equipment 4000 reads out authentication information and time information from the portable data storage 3000 (S12). Here, the relay equipment 4000 may read out authentication information and time information from a single medical information, or may read out authentication information and time information from each of two or more pieces of medical information. Authentication information and time information read out from the same medical information are associated with each other.

The relay equipment 4000 forwards the authentication information and the time information read out from the portable data storage 3000 in the step S12, to the management server 5000 through the telecommunication network 1100 (S13).

The management server 5000 receives the authentication information and the time information sent from the relay equipment 4000 in the step S13. The management server 5000 compares the authentication information with the medical information database 5200 by the authentication information comparison processor 5410 in FIG. 7A (S14). In other words, the authentication information comparison processor 5410 determines whether authentication information corresponding to the authentication information sent from the relay equipment 4000 in the step S13 is stored in the medical information database 5200. In order to do this, the authentication information comparison processor 5410 of some examples compares the authentication information transmitted from the relay equipment 4000 in the step S13 with each authentication information stored in the medical information database 5200, thereby searching for authentication information, from the medical information database 5200, corresponding to the same subject as the authentication information sent from the relay equipment 4000.

If the comparison (authentication information matching) in the step S14 is not successful (S15: No), that is, if the authentication information corresponding to the same subject as the authentication information sent from the relay equipment 4000 is not retrieved from the medical information database 5200, the process moves on to the step S21 of FIG. 10C. Note that the fact that the comparison in the step S14 is not successful means that medical information of this subject has not yet been stored in the medical information database 5200.

On the other hand, if the comparison in the step S14 is successful (S15: Yes), that is, if medical information of this subject has already been stored in the medical information database 5200, the time information comparison processor 5420 compares the time information sent from the relay equipment 4000 in the step S13 with the medical information database 5200 (S16). Here, the time information comparison processor 5420 determines whether time information (examination history) corresponding to the time information sent from the relay equipment 4000 in the step S13 is recorded in the medical information database 5200. In order to do this, the time information comparison processor 5420 of some examples compares the time information sent from the relay equipment 4000 in the step S13 with one or more examination histories associated with the authentication information retrieved from the medical information database 5200 in the step S14, thereby retrieving, from the medical information of this subject, time information corresponding to the time information sent from the relay equipment 4000.

If the comparison (time information matching) in the step S16 is not successful (S17: No), that is, if time information corresponding to the time information sent from the relay equipment 4000 is not retrieved from the medical information of this subject, the process moves on to the step S31 of FIG. 10D. Note that the fact that the comparison in the step S16 is not successful means that examination data of this subject stored in the portable data storage 3000 has not yet been stored in the medical information database 5200.

On the other hand, if the comparison in the step S16 is successful (S17: Yes), that is, if time information corresponding to the time information sent from the relay equipment 4000 is retrieved from the medical information of this subject, the process moves on to the step S41 of FIG. 10E. Note that the fact that the comparison in the step S16 is successful means that examination data of this subject stored in the portable data storage 3000 has already been stored in the medical information database 5200.

Figure 10C:
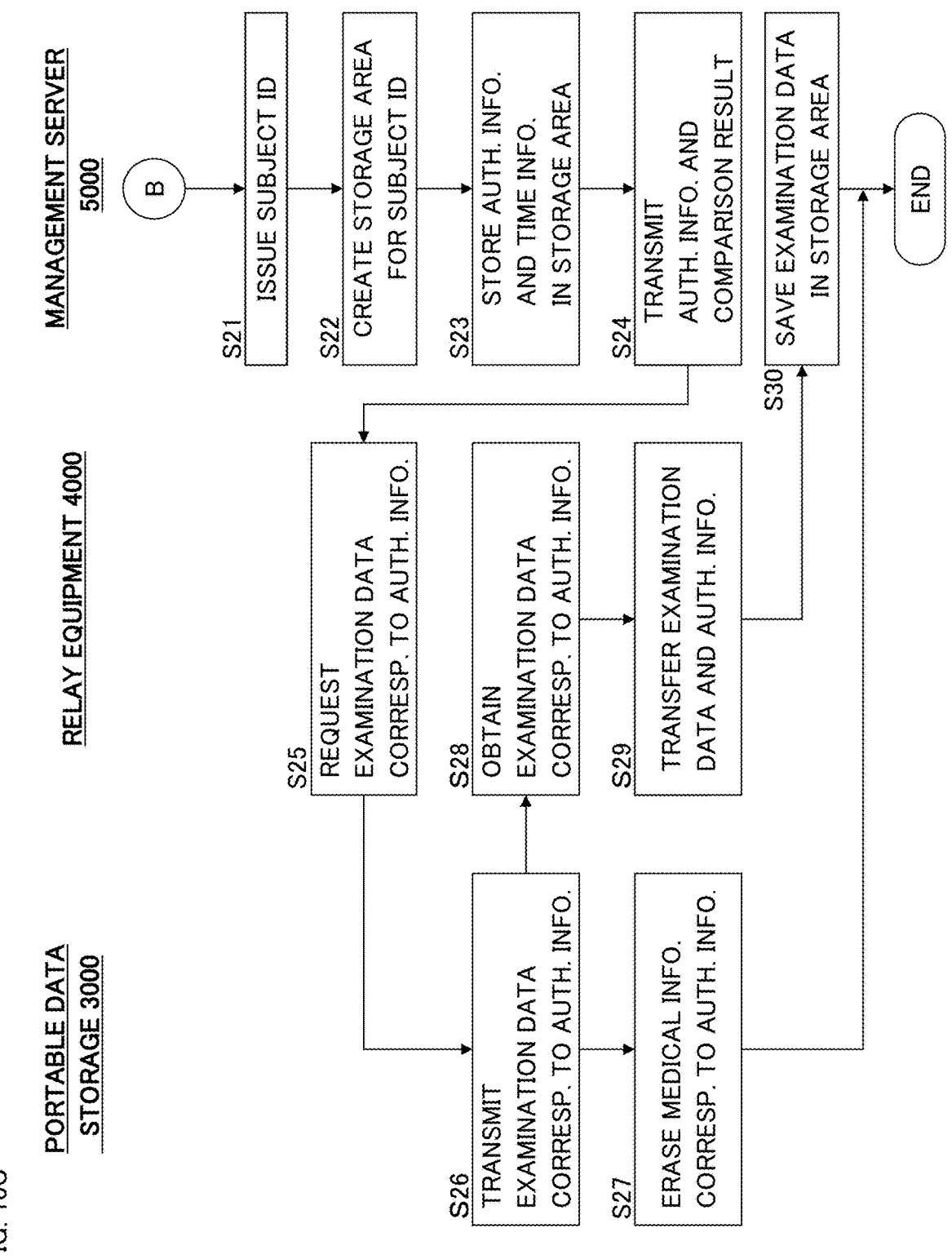
FIG. 10C is a flowchart illustrating the operation of the medical system according to the aspect example.

FIG. 10C is then referred to. The step S21 in FIG. 10C is performed if the comparison of the step S14 is not successful (S15: No), that is, if it is determined that medical information of this subject has not yet been stored in the medical information database 5200.

In the step S21, the management server 5000 issues an identifier for this subject (subject ID). This process is executed, for example, by the controller 5100, the data processor 5400, or the medical information database 5200 (S21).

Next, the management server 5000 creates a storage area in the medical information database 5200 corresponding to the subject ID issued in the step S21. This process is executed, for example, by the controller 5100 or the medical information database 5200 (S22).

Next, the management server 5000 stores the authentication information and the time information sent from the relay equipment 4000 in the step S13 in the storage area created in the step S22 (S23). This process is executed, for example, by the controller 5100 or the medical information database 5200. The time information stored in the medical information database 5200 is used as an examination history.

Next, the management server 5000 transmits the authentication information stored in the storage area corresponding to this subject ID in the step S23 and the results of the comparisons of the steps S14 and S16, to the relay equipment 4000 via the telecommunication network 1100 (S24).

The relay equipment 4000 receives the authentication information and the comparison results sent from the management server 5000 in the step S24. Upon receiving the comparison results (the fact that both the comparison of authentication information and the comparison of time information have failed), the relay equipment 4000 (and/or other elements) performs the process described below.

The relay equipment 4000 makes a request, of the portable data storage 3000, for examination data corresponding to the received authentication information (S25). In response to this request of the step S25, the portable data storage 3000 sends examination data corresponding to this authentication information to the management server 5000 (S26). The relay equipment 4000 or the portable data storage 3000 erases (or, deletes or removes), from the portable data storage 3000, medical information corresponding to the examination data read out by the relay equipment 4000 (S27). The relay equipment 4000 receives the examination data sent from the portable data storage 3000 in the step S26 (S28).

In some examples, the relay equipment 4000 first identifies the same authentication information as the received authentication information, from among a plurality of pieces of authentication information stored in the portable data storage 3000. Then, the relay equipment 4000 reads out, from the portable data storage 3000, examination data associated with this identified authentication information, that is, examination data included in medical information to which the identified authentication information belongs.

The relay equipment 4000 forwards the examination data obtained in the step S28 and this authentication information to the management server 5000 (S29).

The management server 5000 receives the examination data and the authentication information sent from the relay equipment 4000 in the step S29. The management server 5000 compares the received authentication information against a plurality of pieces of authentication information in the medical information database 5200, thereby identifying a storage area corresponding to the received authentication information (see the step S22). The management server 5000 stores, in the identified storage area, the examination data sent from the relay equipment 4000 in the step S29 (S30). In this way, the examination data of this subject can be stored in the storage area in the medical information database 5200 corresponding to this subject. This ends the processes of the present operation example (END).

Note that, in the step S24, the subject ID issued in the step S21 may be sent to the relay equipment 4000 instead of or in addition to the authentication information. If this is the case, the subject ID may be sent to the management server 5000 in the step S29 instead of or in addition to the authentication information. Furthermore, in the step S30, the subject ID can be used to identify the storage area corresponding to this subject.

Figure 10D:
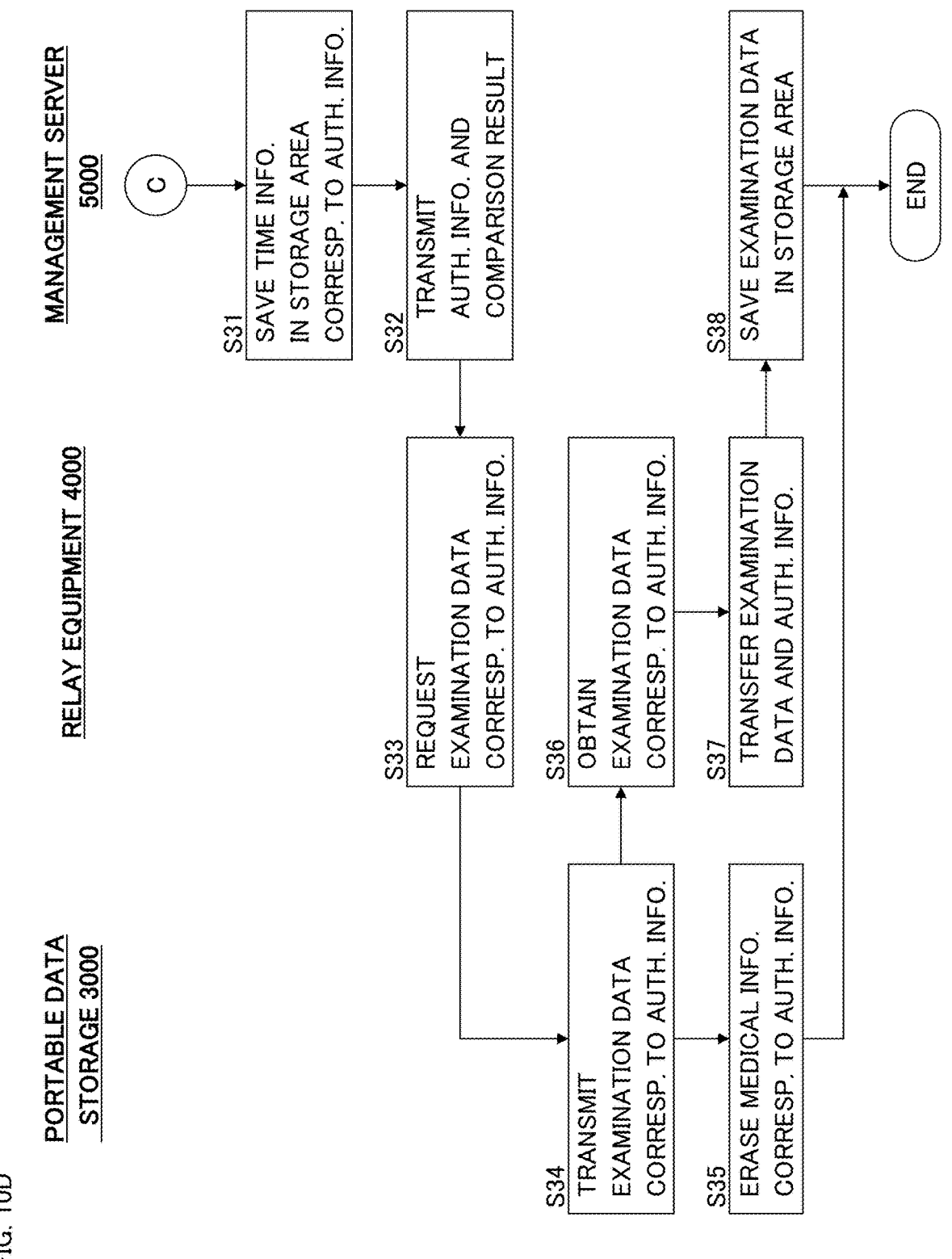
FIG. 10D is a flowchart illustrating the operation of the medical system according to the aspect example.

FIG. 10D is then referred to. The step S31 in FIG. 10D is performed if the comparison of the step S16 is not successful (S17: No), that is, if it is determined that examination data of this subject stored in the portable data storage 3000 has not yet been stored in the medical information database 5200. Note that the storage area corresponding to this subject has already been created in the medical information database 5200.

In the step S31, the management server 5000 of some examples stores the time information sent from the relay equipment 4000 in the step S13 in the storage area corresponding to this subject (S31). This process is executed by the controller 5100 or the medical information database 5200. The time information stored in the medical information database 5200 is used as an examination history.

The authentication information sent from the relay equipment 4000 in the step S13 may be stored in this storage area. In some examples, examination history may be updated with the authentication information sent from the relay equipment 4000 in the step S13. This update of examination history may include, for example, a process of replacing past authentication information (examination history) with new authentication information, or a process of incorporating new authentication information in examination history list.

Next, the management server 5000 transmits the authentication information of this subject and the results of the comparisons of the steps S14 and S16, to the relay equipment 4000 via the telecommunication network 1100 (S32).

The relay equipment 4000 receives the authentication information and the comparison results sent from the management server 5000 in the step S32. Upon receiving the comparison results (the fact that the authentication information comparison has succeeded and the time information comparison has failed), the relay equipment 4000 (and/or other elements) performs the process described below.

The relay equipment 4000 makes a request, of the portable data storage 3000, for examination data corresponding to the received authentication information (S33). In response to this request of the step S33, the portable data storage 3000 sends examination data corresponding to this authentication information to the management server 5000 (S34). The relay equipment 4000 or the portable data storage 3000 erases (or, deletes or removes), from the portable data storage 3000, medical information corresponding to the examination data read out by the relay equipment 4000 (S35). The relay equipment 4000 receives the examination data sent from the portable data storage 3000 in the step S34 (S36).

The relay equipment 4000 forwards the examination data read out from the portable data storage 3000 in the steps S33 to S36 and the authentication information, to the management server 5000 (S37).

The management server 5000 receives the examination data and the authentication information sent from the relay equipment 4000 in the step S37. The management server 5000 compares the received authentication information against a plurality of pieces of authentication information in the medical information database 5200, thereby identifying a storage area corresponding to the received authentication information. The management server 5000 stores, in the identified storage area, the examination data sent from the relay equipment 4000 in the step S37 (S38). In this way, the examination data of this subject can be stored in the storage area in the medical information database 5200 corresponding to this subject. This ends the processes of the present operation example (END).

Note that, in the step S32, the subject ID of this subject may be sent to the relay equipment 4000 instead of or in addition to the authentication information. If this is the case, the subject ID may be sent to the management server 5000 in the step S37 instead of or in addition to the authentication information. Furthermore, in the step S38, the subject ID can be used to identify the storage area corresponding to this subject.

Figure 10E:
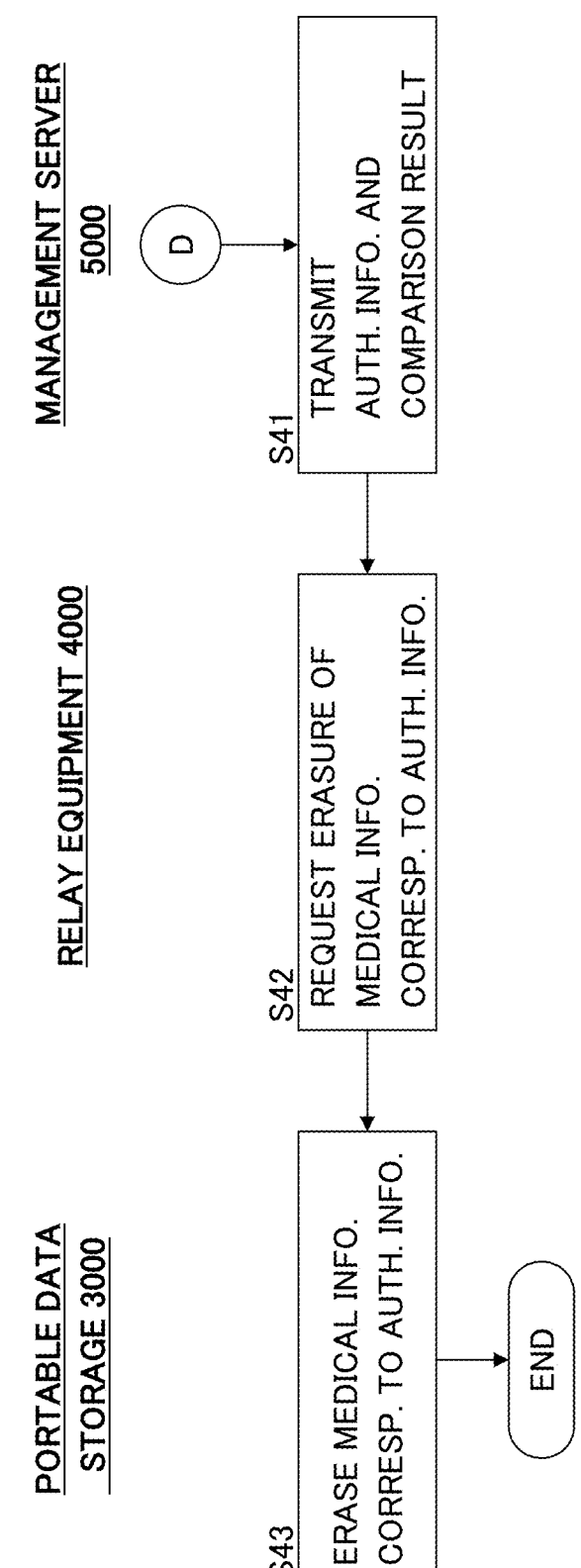
FIG. 10E is a flowchart illustrating the operation of the medical system according to the aspect example.

FIG. 10E is then referred to. The step S41 in FIG. 10E is performed if the comparison of the step S16 is successful (S17: Yes), that is, if it is determined that examination data of this subject stored in the portable data storage 3000 has already been stored in the medical information database 5200. Note that the storage area corresponding to this subject has already been created in the medical information database 5200.

In the step S41, the management server 5000 transmits the authentication information of this subject and the results of the comparisons of the steps S14 and S16, to the relay equipment 4000 via the telecommunication network 1100 (S41).

The relay equipment 4000 receives the authentication information and the comparison results sent from the management server 5000 in the steps S41. Upon receiving the comparison results (the fact that the authentication information comparison has succeeded as well as the time information comparison has succeeded), the relay equipment 4000 (and/or other elements) performs the process described below.

The relay equipment 4000 makes a request, of the portable data storage 3000, for erasure (or, deletion or removal) of medical information corresponding to the received authentication information (S42). In response to this request of the step S42, the portable data storage 3000 erases (or, deletes or removes) the medical information corresponding to this authentication information (S43). This ends the processes of the present operation example (END).

The processes (steps) of the first operation example described above are performed for individual pieces of the medical information (individual pieces of the authentication information) stored in the portable data storage 3000. In other words, any of the processes (any of the steps) of the first operation example is applied one after another to all pieces of the medical information of all subjects stored in the portable data storage 3000.

Figure 11A:
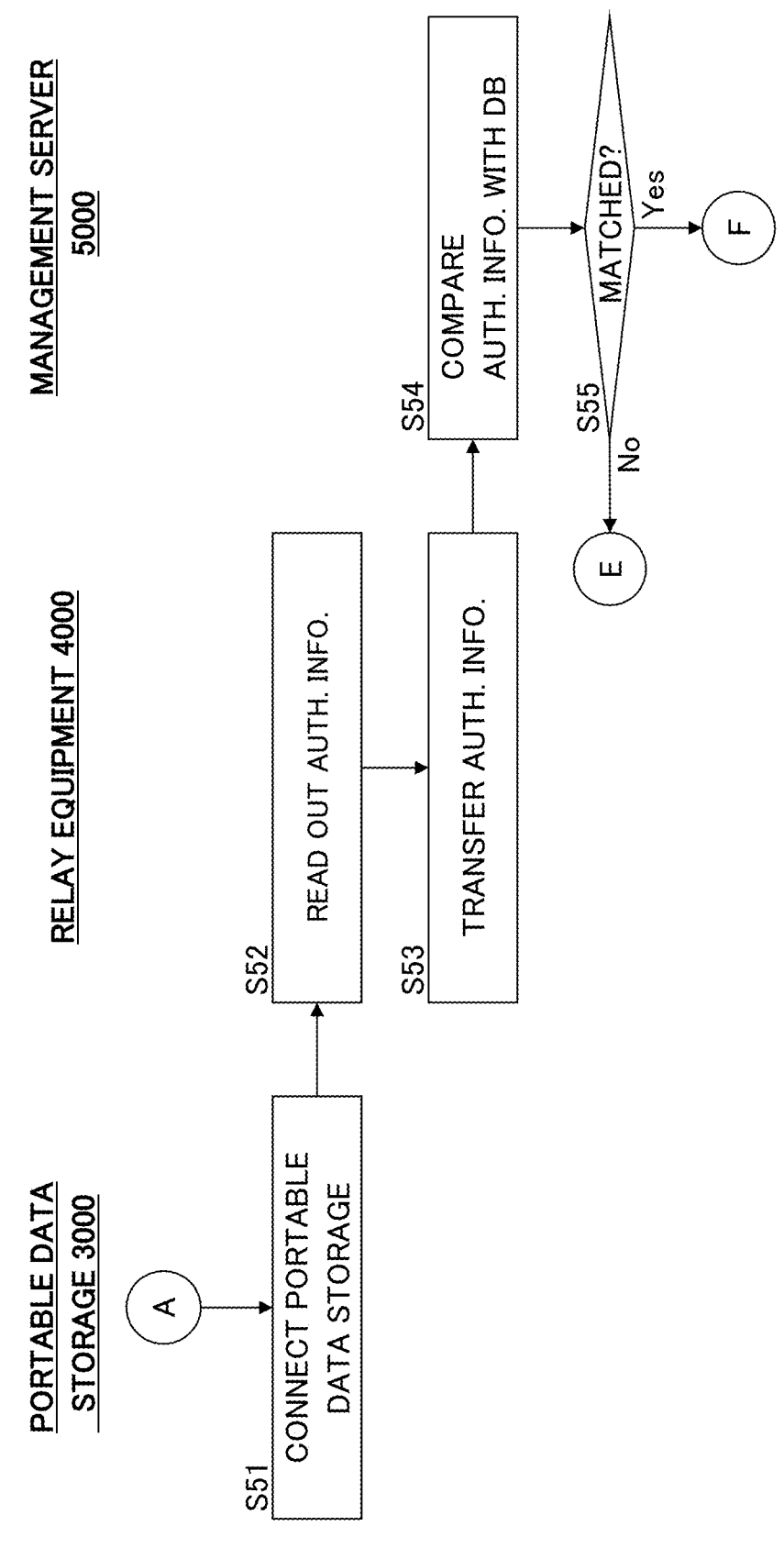
FIG. 11A is a flowchart illustrating the operation of the medical system according to the aspect example.
Figure 11B:
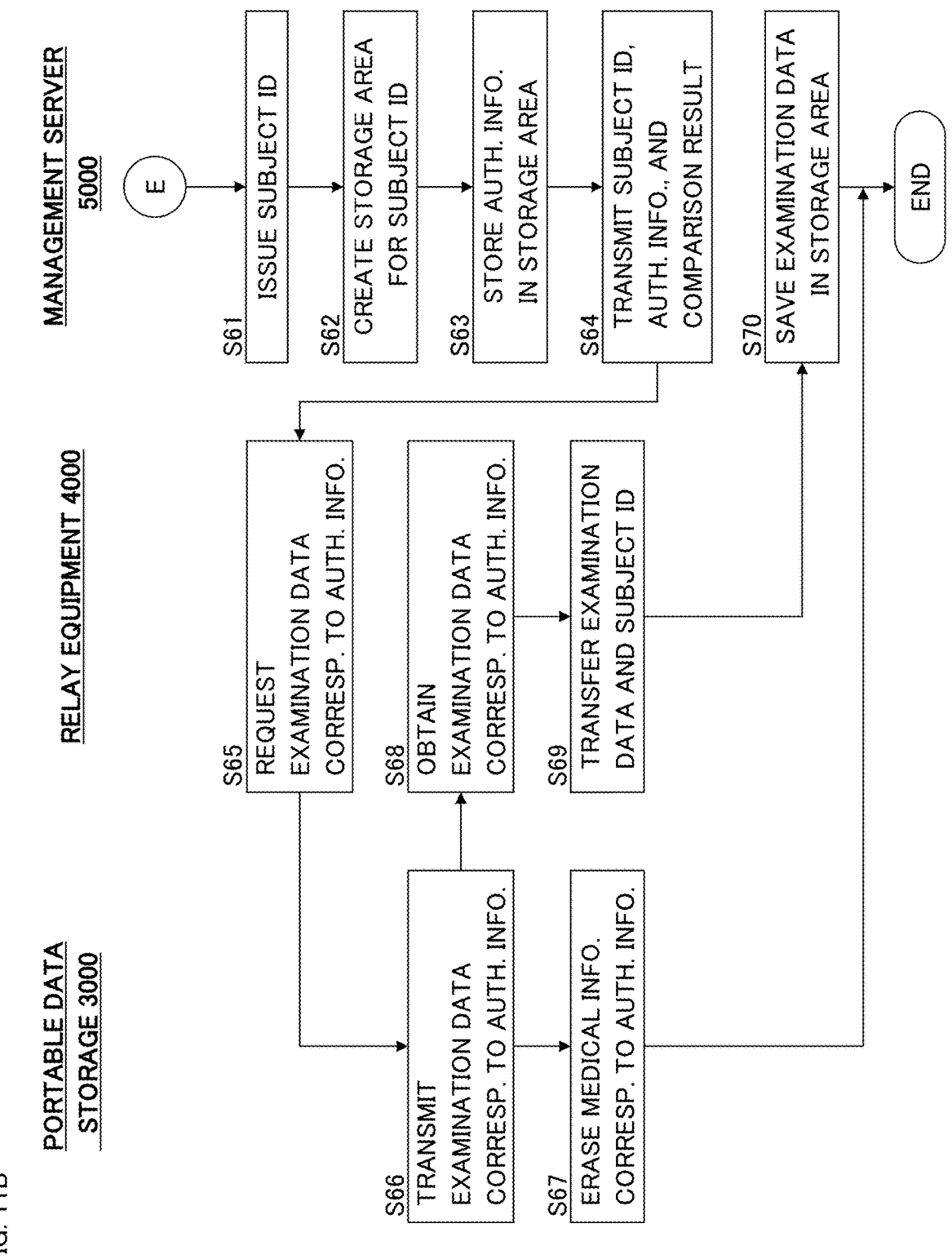
FIG. 11B is a flowchart illustrating the operation of the medical system according to the aspect example.
Figure 11C:
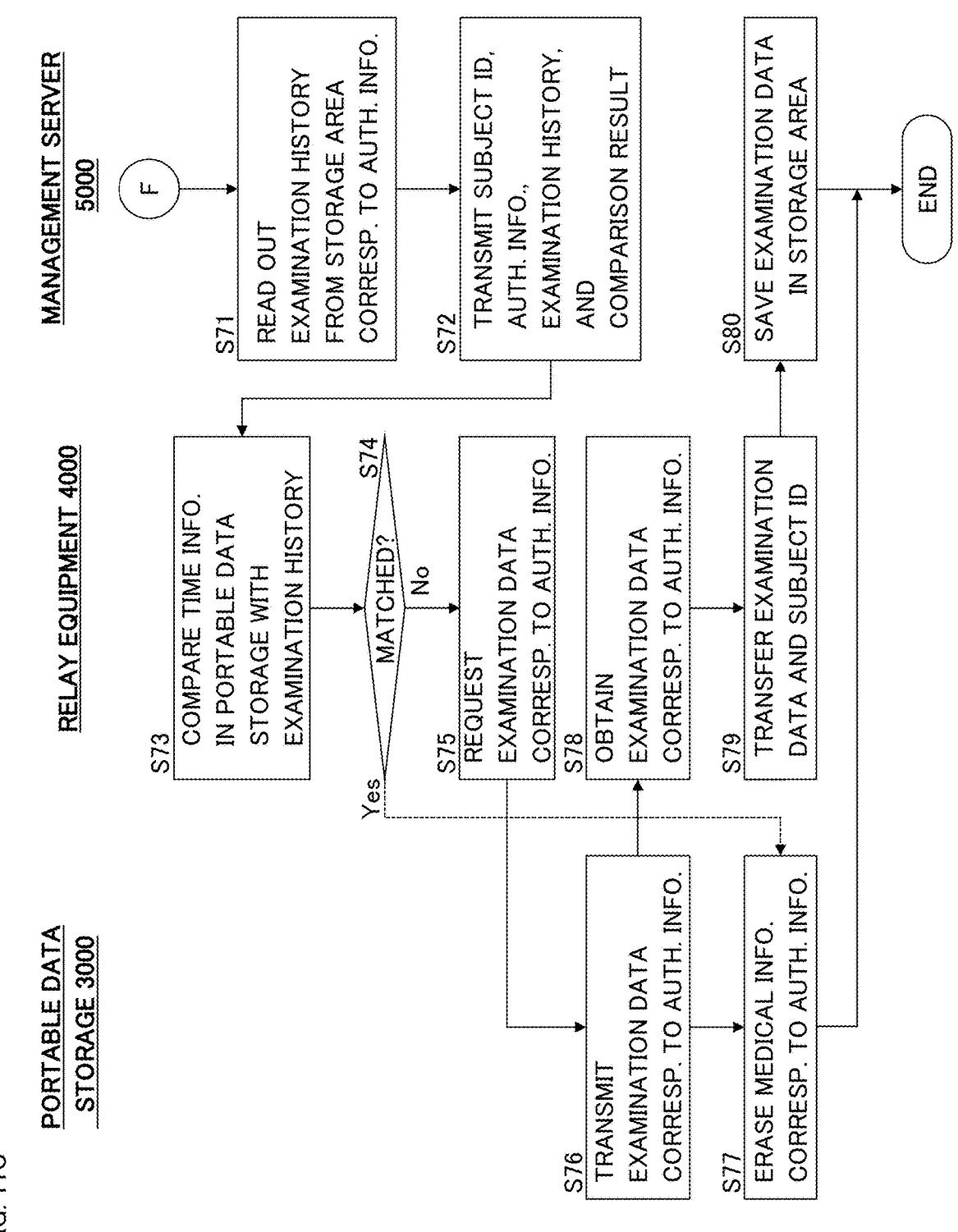
FIG. 11C is a flowchart illustrating the operation of the medical system according to the aspect example.

While the first operation example described above performs both comparison of authentication information and comparison of time information by the management server 5000, the second operation example described below performs comparison of time information (comparison of examination history) by the relay equipment 4000. The second operation example is shown in FIG. 11A to FIG. 11C. Any matters or items freely selected from the first operation example can be applied to the second operation example.

The operation shown in FIG. 11A is performed following the step S6 (FIG. 10A) of the first operation example. First, the portable data storage 3000, in which the medical information collected at the on-site examination sites is stored, is connected to the relay equipment 4000 (S51). The relay equipment 4000 reads out the authentication information from the portable data storage 3000 (S52). The relay equipment 4000 transfers the authentication information read out from the portable data storage 3000 in the step S52, to the management server 5000 via the telecommunication network 1100 (S53).

The management server 5000 receives the authentication information sent from the relay equipment 4000 in the step S53. The management server 5000 compares this authentication information with the medical information database 5200 by the authentication information comparison processor 5410 shown in FIG. 7A (S54).

If the comparison of the step S54 is not successful (S55: No), the operation moves on to the step S61 in FIG. 11B. On the other hand, if the comparison of the step S54 is successful (S55: Yes), the operation moves on to the step S71 in FIG. 11C.

Next, FIG. 11B is referred to. First, the management server 5000 issues an identifier (subject ID) for this subject (S61). Next, the management server 5000 creates a storage area corresponding to this subject ID in the medical information database 5200 (S62). Then, the management server 5000 stores the authentication information sent from the relay equipment 4000 in the step S53, in this newly created storage area corresponding to this subject (S63).

Next, the management server 5000 transmits the subject ID of this subject, the authentication information stored in this storage area in the step S63, and the comparison result obtained by the step S54, to the relay equipment 4000 via the telecommunication network 1100 (S64).

The relay equipment 4000 receives the subject ID, the authentication information, and the comparison verification result sent from the management server 5000 in the step S64. Upon receiving the comparison result (the fact that the authentication information comparison has not succeeded), the relay equipment 4000 (and/or other elements) performs the process described below.

The relay equipment 4000 makes a request, of the portable data storage 3000, for examination data corresponding to the received authentication information (S65). The portable data storage 3000 sends the examination data corresponding to this authentication information to the management server 5000 (S66). The relay equipment 4000 or the portable data storage 3000 erases (or, deletes or removes) the medical information corresponding to this examination data from the portable data storage 3000 (S67). The relay equipment 4000 receives the examination data sent from the portable data storage 3000 in the step S66 (S68).

The relay equipment 4000 forwards the examination data acquired in the step S28 and the subject ID to the management server 5000 (S69). The authentication information may be sent instead of or in addition to the subject ID.

The management server 5000 receives the examination data and the subject ID sent from the relay equipment 4000 in the step S69. The management server 5000 identifies the storage area in the medical information database 5200 corresponding to the received subject ID. The management server 5000 saves the examination data sent from the relay equipment 4000 in the step S69 in the identified storage area (S70). In this way, the examination data of this subject can be stored in the storage area in the medical information database 5200 corresponding to this subject. This ends the processes of the present operation example (END).

In some examples, the time information and the examination data corresponding to the authentication information may be read out from the portable data storage 3000 in the step S68, transmission of the time information, the examination data and the subject ID (and/or the authentication information) may be performed in the step S69, and storage of the time information and the examination data may be performed in the step S70. In some examples, addition or update of examination history may be performed in the step S70.

FIG. 11C is now referred to. First, the management server 5000 reads out the examination history from the storage area corresponding to this subject (S71). Next, the management server 5000 transmits the subject ID of this subject, the authentication information of this subject, the examination history read out in the step S71, and the comparison result obtained in the step S54, to the relay equipment 4000 via the telecommunication network 1100 (S72).

The relay equipment 4000 receives the subject ID, the authentication information, the examination history, and the comparison result sent from the management server 5000 in the step S72. Upon receiving the comparison result (the fact that the authentication information comparison has succeeded), the relay equipment 4000 (and/or other elements) performs the process described below.

The relay equipment 4000 performs, by the time information comparison processor 4420, comparison between the examination history sent from the management server 5000 in the step S72 and the time information stored in the portable data storage 3000 (S73). In some examples, the relay equipment 4000 identifies the time information corresponding to this subject based on the received authentication information, and then performs comparison between the identified time information and this examination history.

If the comparison of the step S73 is not successful (S74: No), the operation moves on to the step S75. On the other hand, if the comparison of the step S73 is successful (S74: Yes), the operation moves on to the step S77.

If the comparison of the step S73 is successful (S74: Yes), the relay equipment 4000 or the portable data storage 3000 erases (or, deletes or removes) the medical information corresponding to the examination data corresponding to this authentication information, from the portable data storage 3000 (S77).

On the other hand, if the comparison of the step S73 is not successful (S74: No), the relay equipment 4000 makes a request, of the portable data storage 3000, for examination data corresponding to the received authentication information (S75). In response to this request of the step S75, the portable data storage 3000 sends examination data corresponding to this authentication information to the management server 5000 (S76). The relay equipment 4000 or the portable data storage 3000 erases (or, deletes or removes), from the portable data storage 3000, medical information corresponding to the examination data read out by the relay equipment 4000 (S77). The relay equipment 4000 receives the examination data sent from the portable data storage 3000 in the step S76 (S78).

The relay equipment 4000 forwards the examination data read out from the portable data storage 3000 in the steps S75 to S78 and the subject ID, to the management server 5000 (S79).

The management server 5000 receives the examination data and the subject ID sent from the relay equipment 4000 in the step S79. The management server 5000 identifies the storage area of this subject based on the received subject ID, and stores the examination data sent from the relay equipment 4000 in the step S79 in the identified storage area (S80). In this way, the examination data of this subject can be stored in the storage area in the medical information database 5200 corresponding to this subject. This ends the processes of the present operation example (END).

In some examples, the time information and the examination data corresponding to the authentication information may be read out from the portable data storage 3000 in the step S78, transmission of the time information, the examination data and the subject ID (and/or the authentication information) may be performed in the step S79, and storage of the time information and the examination data may be performed in the step S80. In some examples, addition or update of examination history may be performed in the step S80.

The processes (steps) of the second operation example described above are performed for individual pieces of the medical information (individual pieces of the authentication information) stored in the portable data storage 3000. In other words, any of the processes (any of the steps) of the second operation example is applied one after another to all pieces of the medical information of all subjects stored in the portable data storage 3000.

The first or second operation example makes it possible to ascertain (verify, check) whether examination data obtained from a subject on the same examination date is already stored in the medical information database 5200. In addition to this, the first or second operation example makes it possible to transmit, only when such examination data is not yet stored in the medical information database 5200, examination data newly acquired from this subject to the management server 5000 via the relay equipment 4000.

By performing such processes for individual pieces of the authentication information retained in the portable data storage 3000, it becomes possible, for individual pieces of examination data stored in the portable data storage 3000, to ascertain (verify, check) whether examination data of the same subject and the same examination date is already stored in the medical information database 5200, and to store only examination data that has not yet been stored in the medical information database 5200 in the medical information database 5200. Therefore, the medical information database 5200 can be constructed (configured, formed) with no omissions and no duplication on both a subject basis and an examination-date basis. In this way, the technology (technique, method) achieved and provided by the present aspect example contributes to improvement in on-site examinations conducted in areas with poor network environments.

It is considered that there may be cases where medical information that is not subject to the processes of the first or second operation example is stored in the portable data storage 3000. It may be possible to erase (or, delete or remove) such medical information; however, it may also be possible to leave such medical information in the portable data storage 3000 without erasing it, or to store such medical information in other devices (e.g., the relay equipment 4000 or its peripheral equipment).

In the first and second operation examples, information stored in the portable data storage 3000 is read and processed one after another. In some typical examples, the first and second examples read and process a plurality of pieces of medical information stored in the portable data storage 3000 one after another on a subject basis.

However, the medical system 1000 of some other examples may be configured to read out all medical information stored in the portable data storage 3000 and then perform processing of it. If this is the case, for example, all data stored in the portable data storage 3000 may be transferred (migrated) to the relay equipment 4000 or its peripheral equipment. After completion of the migration of all the data in the portable data storage 3000, the connection between the relay equipment 4000 and the portable data storage 3000 is released. All the migrated data is then erased (deleted) from the portable data storage 3000. After that, for example, the processes after the step S13 in FIG. 108 (the first operation example) or the processes after the step S53 in FIG. 11A (the second operation example) are performed.

<Second aspect> In the first aspect described above, the data stored in the portable data storage 3000 is sent to the management server 5000 via the relay equipment 4000. However, some aspect examples do not employ the relay equipment 4000. The present aspect describes some examples of the medical system is such aspect examples. Note that any matters or items of the first aspect example may be combined with or incorporated in the present aspect examples.

Figure 12:
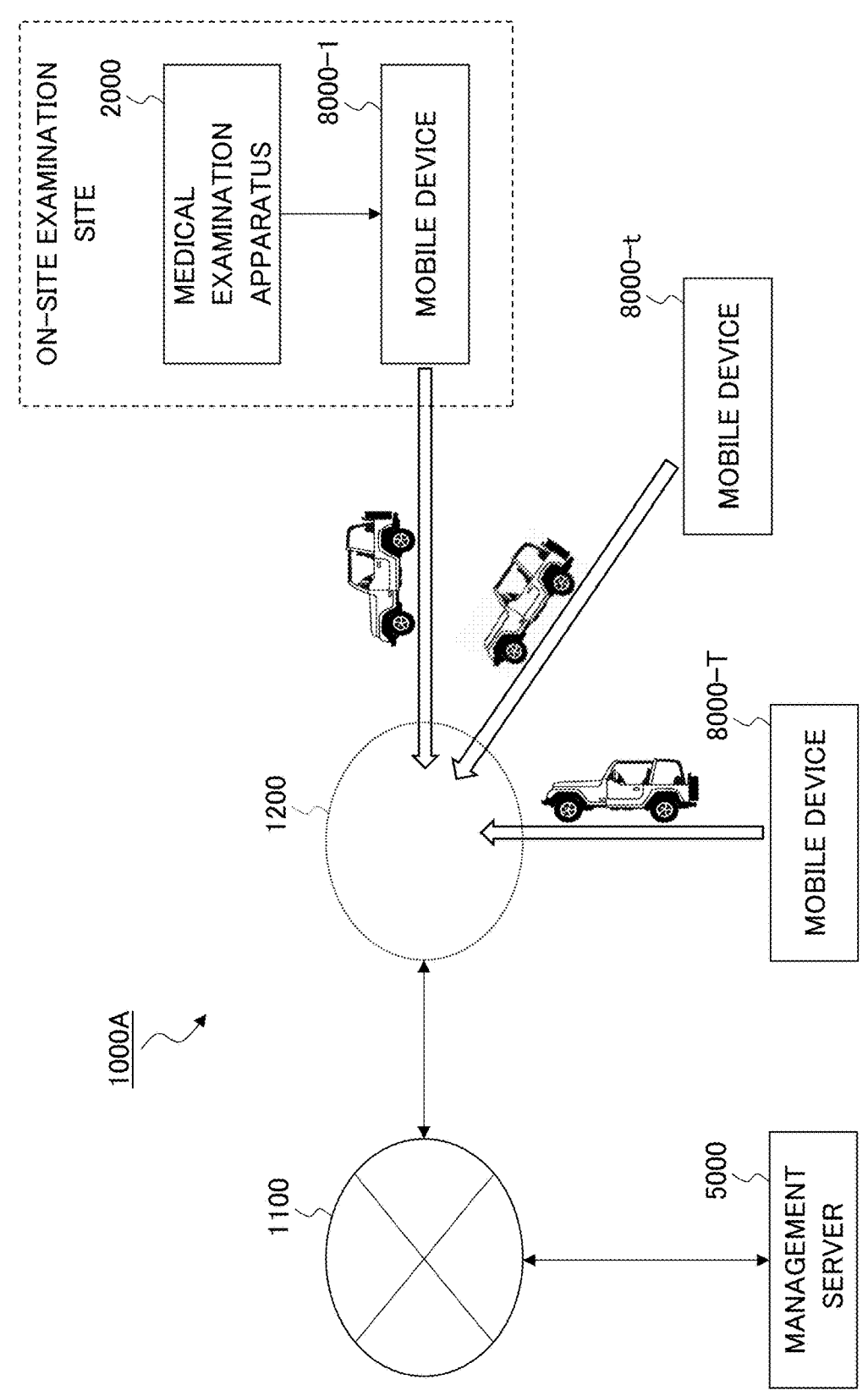
FIG. 12 is a schematic diagram illustrating the configuration of the medical system according to the aspect example.

The medical system 1000A shown in FIG. 12 includes the T pieces of portable data storage 8000-t, and the management server 5000 having the same or similar functions and configurations as or to the first aspect. Here, the number "T" is a positive integer greater than or equal to 1, and "t" is a positive integer less than or equal to "T". In the following, any one of the T pieces of portable data storage 8000-t is sometimes denoted by the reference character "8000". The medical system 1000A may further include the medical examination apparatus 2000.

The area denoted by the reference character "1200" is the available area of the telecommunication network 1100. In the present example, typically, a wireless connection to the telecommunication network 1100 can be established within the available area 1200. The mobile device 8000 situated in the available area 1200 can perform data communication with the management server 5000 via the telecommunication network 1100.

Figure 13:
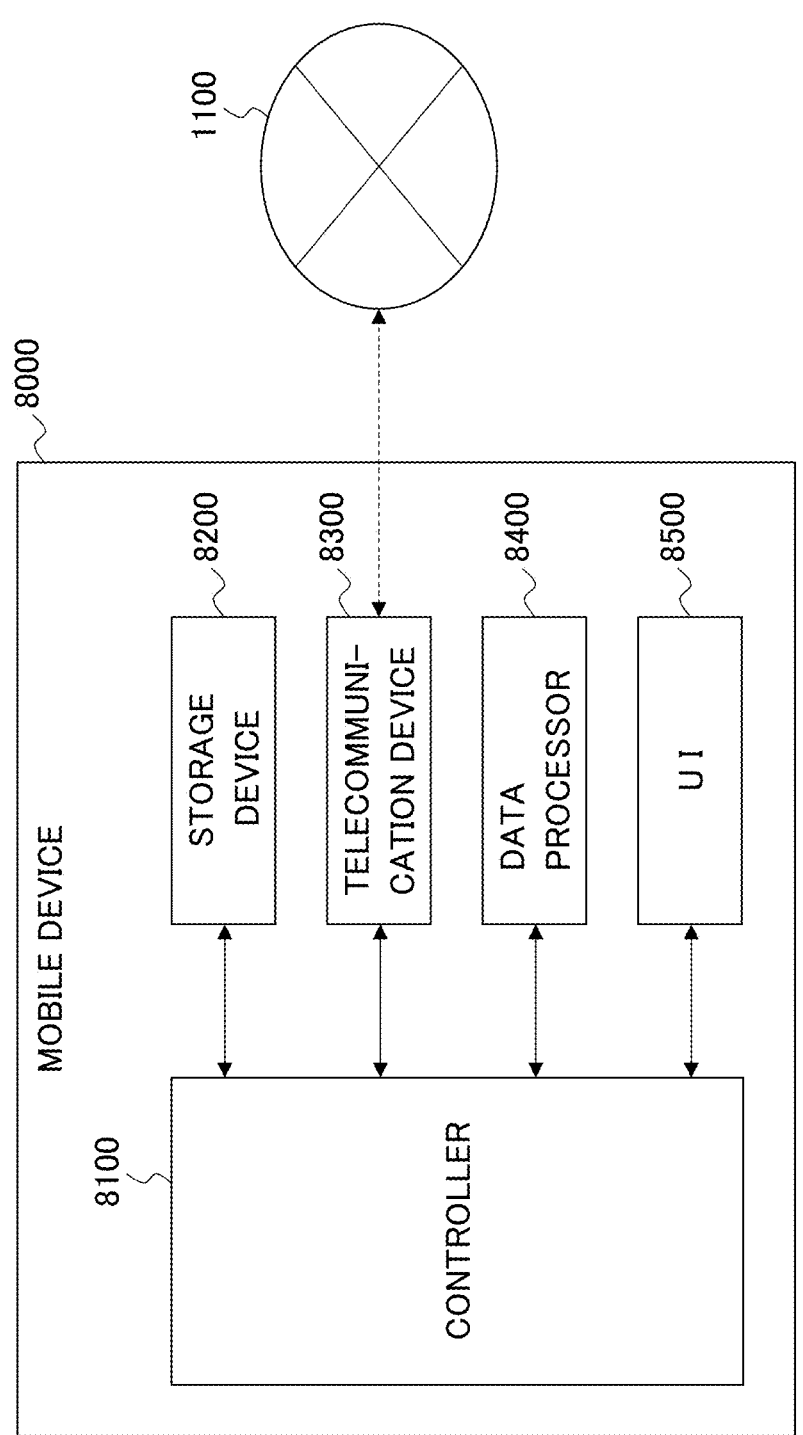
FIG. 13 is a schematic diagram illustrating the configuration of the medical system according to the aspect example.

An example of the configuration of the mobile device 8000 is shown in FIG. 13. The mobile device 8000 of the present example includes the controller 8100, the storage device 8200, the telecommunication device 8300, the data processor 8400, and the user interface (UI) 8500. The mobile device 8000 of some examples may be a tablet computer, a smartphone, a laptop computer, or the like.

The controller 8100 controls each part of the mobile device 8000. The controller 8100 includes a processor, a primary storage, a secondary storage, and the like. The secondary storage retains a control program. The control program may be stored in a computer or a storage to which the mobile device 8000 can access. The functions of the controller 8100 are implemented by cooperation of software such as the control program and hardware such as the processor. The controller 8100 may have the same or similar functions and configuration as or to the controller 4100 of the relay equipment 4000 in the first aspect.

The storage device 8200 is an alternative to the portable data storage 3000 of the first aspect. The storage device 8200 retains medical information that includes at least authentication information of a subject who has undergone a medical examination using the medical examination apparatus 2000 and examination data obtained from the subject by this medical examination. The medical information may further include time information corresponding to the medical examination.

The telecommunication device 8300 includes a communication device configured to perform data communication through the telecommunication network 1100.

The data processor 8400 performs various data processing. The data processor 8400 includes a processor, a primary storage, a secondary storage, and the like. The secondary storage retains a data processing program. The data processing program may be stored in a computer or a storage to which the mobile device 8000 can access. The functions of the data processor 8400 are implemented by cooperation of software such as the data processing program and hardware such as the processor.

The data processor 8400 may include any one or more of the authentication information comparison processor, the time information comparison processor, the authentication information generation processor, and the time information generation processor. Each of these elements may have the same or similar functions and configuration as or to its corresponding element in the first aspect. The data processor 8400 may have the same or similar functions and configuration as or to the data processor 4400 of the relay equipment 4000 in the first aspect.

The user interface 8500 includes a display device, an operation device, and the like.

Figure 14:
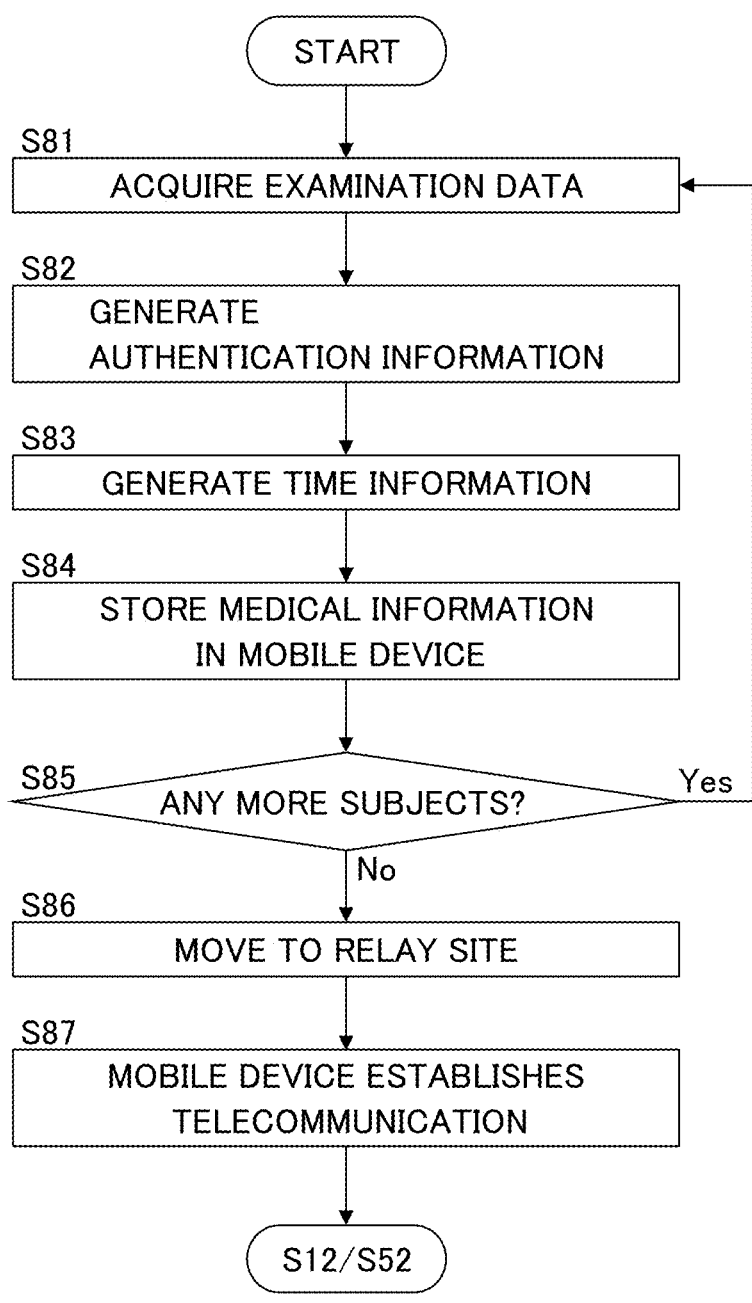
FIG. 14 is a flowchart illustrating the operation of the medical system according to the aspect example.

The operation of the medical system 1000A is now described. FIG. 14 illustrates an example of the operation of the medical system 1000A. The series of steps (processes) shown in FIG. 14 is performed in place of the series of steps (processes) shown in FIG. 10A of the first aspect, for example.

In some examples, an examiner(s) travels to an on-site examination site by a vehicle on which the medical examination apparatus 2000 (the slit lamp microscope 1) and the mobile device 8000 are loaded. The examiner may also carry the time information generation device 6000 and/or the authentication information generation device 7000.

At the on-site examination site, the examiner conducts examinations on subjects using the medical examination apparatus 2000, thereby acquiring examination data for individual subjects (S81). In addition, generation of authentication information (S82) and generation of time information (S83) are performed for individual subjects. The timings and the order of the examination data acquisition, the authentication information generation, and the time information generation may be freely determined.

The medical examination apparatus 2000 or the mobile device 8000 can manage examination data, authentication information, and time information for a subject as medical information for this subject. The medical information of each subject obtained in this way is stored in the storage device 8200 of the mobile device 8000 (S84).

The steps S81 to S84 are repeated until medical information is obtained for all subjects at the on-site examination site (S85: Yes). After medical information for all of the subjects has been obtained (S85: No), the examiner puts the medical examination apparatus 2000, the mobile device 8000, etc. into the vehicle and travels to a relay site (S86). The relay site is a place from which the medical information stored in the mobile device 8000 is transmitted to the management server 5000. The relay site of the present aspect example may be any kind of site located within the available area 1200. The examiner may come to the relay site via other one or more on-site examination sites. In this case, the processes of the steps S81 to S85 are performed also at each of the one or more on-site examination sites.

After the mobile device 8000, which retains the medical information collected at the on-site examination site, enters the relay site, the mobile device 8000 establishes communication with the management server 5000 through the telecommunication network 1100 (S87). After this communication establishment, the operation of the present example moves on to the step S12 of FIG. 10B or the step S52 of FIG. 11A in the first aspect. The processes performed in the step S12 or the S52 and thereafter may be the same as those in the first aspect.

As with the first aspect, the technology (technique, method) achieved and provided by the present aspect example contributes to improvement in on-site examinations conducted in areas with poor network environments.

Some aspects described above are merely examples of the implementation of the present disclosure, and any modifications (e.g., omission, substitution, replacement, addition, etc.) may be made within the scope of the present disclosure to the above aspect examples.

What is claimed is:

1. A medical system comprising:
   a medical examination apparatus configured to perform an on-site medical examination on each of a plurality of subjects to acquire examination data for individual subjects, the on-site medical examination being conducted in an on-site examination site located in a first region outside of a second region, the first region having a poorer telecommunication network environment than the second region;
   a time information generation device including a timer configured to generate time information corresponding to the on-site medical examination for individual subjects in the on-site examination site, the time information including a date of conducting the on-site medical examination;
   an authentication information generation device including a computer configured to generate authentication information corresponding to the on-site medical examination for individual subjects in the on-site examination site, the authentication information including biometrics information;
   portable data storage including memory configured to store the examination data, the time information, and the authentication information at the on-site examination site;
   a management server including a computer and a medical information database to manage examination data, time information, and authentication information; and
   a relay equipment including a computer located in the second region, connected to the portable data storage, and configured to read out time information and authentication information of a subject from the portable data storage and transfer the time information and the authentication information read out to the management server, wherein
   one or both of the computer of the relay equipment and the computer of the management server is configured to compare the time information and the authentication information of the subject with the medical information database to perform time information matching and authentication information matching,
   the time information, the authentication information, and examination data of the subject are erased from the portable data storage based on both the time information matching and the authentication information matching being successful,
   the computer of the relay equipment includes a communication controller and a readout controller, the communication controller being configured to automatically establish a telecommunication connection between the portable data storage and the management server through the relay equipment when the portable data storage is moved from the first region to the second region and transitions from a state in which the telecommunication network is unavailable to a state in which the telecommunication network is available, and the readout controller being configured to read out the time information and the authentication information from the portable data storage in response to establishment of the telecommunication connection,
   one or both of the computer of the relay equipment and the computer of the management server includes a first comparison processor and a second comparison processor, the first comparison processor being configured to perform the authentication information matching, and the second comparison processor being configured to perform the time information matching,
   the computer of the relay equipment includes a transfer controller configured to acquire the examination data from the portable data storage and transmit the acquired examination data to the management server only when at least one of the first comparison processor and the second comparison processor determines that corresponding information is absent in the medical information database, and
   erasure of the time information, the authentication information, and the examination data is performed in response to acquisition of the examination data by the transfer controller.

2. The medical system of claim 1, wherein if the authentication information matching is not successful, the management server issues an identifier of the subject, creates a storage area in the medical information database corresponding to the identifier issued for the subject, and stores the authentication information and the time information of the subject transmitted from the relay equipment into the storage area,
   the portable data storage transmits the examination data of the subject to the relay equipment,
   the relay equipment transmits the examination data of the subject transmitted from the portable data storage to the management server, and
   the management server stores the examination data of the subject transmitted from the relay equipment into the storage area corresponding to the identifier of the subject.

3. The medical system of claim 2, wherein the examination data, the time information, and the authentication information of the subject are erased from the portable data storage after the portable data storage transmits the examination data of the subject to the relay equipment.

4. The medical system of claim 1, wherein if the authentication information matching is successful and the time information matching is not successful, the management server stores the time information of the subject transmitted from the relay equipment into a storage area in the medical information database previously created for the subject, the portable data storage transmits the examination data of the subject to the relay equipment, the relay equipment transmits the examination data of the subject transmitted from the portable data storage to the management server, and the management server stores the examination data of the subject transmitted from the relay equipment into the storage area of the subject.

5. The medical system of claim 4, wherein the examination data, the time information, and the authentication information of the subject are erased from the portable data storage after the portable data storage transmits the examination data of the subject to the relay equipment.

6. The medical system of claim 1, wherein the on-site examination includes treatment for a medical condition of at least one of the plurality of subjects.

7. The medical system of claim 6, wherein the medical condition includes a cataract.

8. The medical system of claim 1, wherein the medical examination apparatus includes one or more of a slit lamp microscope, a fundus camera, a scanning laser ophthalmoscope (SLO), an ocular refractometer, an ocular keratometer, a tonometer, a specular microscope, a wave front analyzer, an ocular axial length measurement apparatus, a visual field measurement apparatus, and an optical coherence tomography (OCT) apparatus.

\* \* \* \* \*